(12) United States Patent
Lee

(10) Patent No.: US 11,446,504 B1
(45) Date of Patent: Sep. 20, 2022

(54) HIGH FREQUENCY ELECTROMAGNETIC STIMULATION FOR MODULATING CELLS, INCLUDING SPONTANEOUSLY ACTIVE AND QUIESCENT CELLS, AND ASSOCIATED SYSTEMS AND METHODS

(71) Applicant: Nevro Corp., Redwood City, CA (US)

(72) Inventor: Dongchul Lee, Agua Dulce, CA (US)

(73) Assignee: Nevro Corp., Redwood City, CA (US)

( * ) Notice: Subject to any disclaimer, the term of this patent is extended or adjusted under 35 U.S.C. 154(b) by 1282 days.

(21) Appl. No.: 15/606,869

(22) Filed: May 26, 2017

Related U.S. Application Data

(60) Provisional application No. 62/342,855, filed on May 27, 2016.

(51) Int. Cl.
*A61N 1/36* (2006.01)
*A61N 1/08* (2006.01)

(52) U.S. Cl.
CPC ........... *A61N 1/36128* (2013.01); *A61N 1/08* (2013.01); *A61N 1/36103* (2013.01)

(58) Field of Classification Search
None
See application file for complete search history.

(56) References Cited

U.S. PATENT DOCUMENTS

| | | |
|---|---|---|
| 1,597,061 A | 8/1926 | Cultra |
| 2,622,601 A | 12/1952 | Nemec |
| 3,195,540 A | 7/1965 | Waller |
| 3,817,254 A | 6/1974 | Maurer |
| 3,822,708 A | 7/1974 | Zilber |
| 3,893,463 A | 7/1975 | Williams |
| 4,014,347 A | 3/1977 | Halleck et al. |
| 4,023,574 A | 5/1977 | Nemec |
| 4,055,190 A | 10/1977 | Tany et al. |
| 4,414,986 A | 11/1983 | Dickhudt et al. |
| 4,535,777 A | 8/1985 | Castel |
| 4,541,432 A | 9/1985 | Molina-Negro et al. |

(Continued)

FOREIGN PATENT DOCUMENTS

| | | |
|---|---|---|
| GB | 2449546 A | 11/2008 |
| JP | 2007528774 A | 10/2007 |

(Continued)

OTHER PUBLICATIONS

Alo et al., "New Trends in Neuromodulation for the Management of Neuropathic Pain," Neurosurgery, vol. 50, No. 4, Apr. 2002, 15 pages.

(Continued)

*Primary Examiner* — Michael W Kahelin
*Assistant Examiner* — Elizabeth K So
(74) *Attorney, Agent, or Firm* — Perkins Coie LLP

(57) ABSTRACT

Electromagnetic stimulation for treating diseases, conditions associated with diseases and/or inhibiting pain with reduced side effects and associated systems and methods are disclosed. In particular embodiments, high-frequency stimulation in the range of from about 1.5 kHz to about 100 kHz may be applied to a patient's target tissue region to treat the disease, associated condition and/or to inhibit pain. Electrical stimulation in accordance with similar parameters can directly affect a cellular membrane, such as a neuron and in particular, a spontaneously active neuron and/or a quiescent neuron.

27 Claims, 23 Drawing Sheets

(56) References Cited

U.S. PATENT DOCUMENTS

| | | |
|---|---|---|
| 4,608,985 A | 9/1986 | Crish et al. |
| 4,649,935 A | 3/1987 | Charmillot et al. |
| 4,841,973 A | 6/1989 | Stecker |
| RE33,420 E | 11/1990 | Sussman et al. |
| 5,002,053 A | 3/1991 | Garcia-Rill |
| 5,335,657 A | 8/1994 | Terry, Jr. et al. |
| 5,354,320 A | 10/1994 | Schaldach et al. |
| 5,514,175 A | 5/1996 | Kim et al. |
| 5,562,717 A | 10/1996 | Tippey et al. |
| 5,643,330 A | 7/1997 | Holsheimer et al. |
| 5,776,170 A | 7/1998 | MacDonald et al. |
| 5,806,522 A | 9/1998 | Katims |
| 5,830,151 A | 11/1998 | Hadzic et al. |
| 5,853,373 A | 12/1998 | Griffith et al. |
| 5,893,883 A | 4/1999 | Torgerson |
| 5,983,141 A | 11/1999 | Sluijter et al. |
| 5,995,872 A | 11/1999 | Bourgeois |
| 6,002,964 A | 12/1999 | Feler et al. |
| 6,014,588 A | 1/2000 | Fitz |
| 6,027,456 A | 2/2000 | Feler et al. |
| 6,161,044 A | 12/2000 | Silverstone |
| 6,167,311 A | 12/2000 | Rezai |
| 6,176,242 B1 | 1/2001 | Rise |
| 6,233,488 B1 | 5/2001 | Hess |
| 6,238,423 B1 | 5/2001 | Bardy |
| 6,246,912 B1 | 6/2001 | Sluijter et al. |
| 6,341,236 B1 | 1/2002 | Osorio et al. |
| 6,356,786 B1 | 3/2002 | Rezai et al. |
| 6,405,079 B1 | 6/2002 | Ansarinia |
| 6,421,566 B1 | 7/2002 | Holsheimer |
| 6,440,090 B1 | 8/2002 | Schallhorn |
| 6,505,078 B1 | 1/2003 | King et al. |
| 6,510,347 B2 | 1/2003 | Borkan |
| 6,571,127 B1 | 5/2003 | Ben-Haim et al. |
| 6,584,358 B2 | 6/2003 | Carter et al. |
| 6,609,030 B1 | 8/2003 | Rezai et al. |
| 6,622,048 B1 | 9/2003 | Mann |
| 6,721,603 B2 | 4/2004 | Zabara et al. |
| 6,795,737 B2 | 9/2004 | Gielen et al. |
| 6,871,090 B1 | 3/2005 | He et al. |
| 6,885,888 B2 | 4/2005 | Rezai |
| 6,907,295 B2 | 6/2005 | Gross et al. |
| 6,923,784 B2 | 8/2005 | Stein |
| 6,928,320 B2 | 8/2005 | King |
| 6,950,707 B2 | 9/2005 | Whitehurst |
| 6,968,237 B2 | 11/2005 | Doan et al. |
| 6,990,376 B2 | 1/2006 | Tanagho et al. |
| 7,024,246 B2 | 4/2006 | Acosta et al. |
| 7,047,079 B2 | 5/2006 | Erickson |
| 7,082,333 B1 | 7/2006 | Bauhahn et al. |
| 7,117,034 B2 | 10/2006 | Kronberg |
| 7,146,224 B2 | 12/2006 | King |
| 7,149,574 B2 | 12/2006 | Yun et al. |
| 7,167,750 B2 | 1/2007 | Knudson et al. |
| 7,174,215 B2 | 2/2007 | Bradley |
| 7,180,760 B2 | 2/2007 | Varrichio et al. |
| 7,206,632 B2 | 4/2007 | King |
| 7,212,865 B2 | 5/2007 | Cory |
| 7,236,822 B2 | 6/2007 | Dobak, III |
| 7,239,912 B2 | 7/2007 | Dobak, III |
| 7,252,090 B2 | 8/2007 | Goetz |
| 7,260,436 B2 | 8/2007 | Kilgore et al. |
| 7,266,412 B2 | 9/2007 | Stypulkowski |
| 7,288,062 B2 | 10/2007 | Spiegel |
| 7,313,440 B2 | 12/2007 | Miesel |
| 7,324,852 B2 | 1/2008 | Barolat et al. |
| 7,326,181 B2 | 2/2008 | Katims |
| 7,333,857 B2 | 2/2008 | Campbell |
| 7,337,005 B2 | 2/2008 | Kim et al. |
| 7,346,398 B2 | 3/2008 | Gross et al. |
| 7,349,743 B2 | 3/2008 | Tadlock |
| 7,363,076 B2 | 4/2008 | Yun et al. |
| 7,389,145 B2 | 6/2008 | Kilgore et al. |
| 7,393,351 B2 | 7/2008 | Woloszko et al. |
| 7,493,172 B2 | 2/2009 | Whitehurst et al. |
| 7,502,652 B2 | 3/2009 | Gaunt et al. |
| 7,580,753 B2 | 8/2009 | Kim et al. |
| 7,599,737 B2 | 10/2009 | Yomtov et al. |
| 7,676,269 B2 | 3/2010 | Yun et al. |
| 7,689,289 B2 | 3/2010 | King |
| 7,734,340 B2 | 6/2010 | De Ridder |
| 7,742,810 B2 | 6/2010 | Moffitt et al. |
| 7,761,170 B2 | 7/2010 | Kaplan et al. |
| 7,778,704 B2 | 8/2010 | Rezai |
| 7,813,803 B2 | 10/2010 | Heruth et al. |
| 7,826,901 B2 | 11/2010 | Lee et al. |
| 7,860,570 B2 | 12/2010 | Whitehurst et al. |
| 7,877,136 B1 * | 1/2011 | Moffitt ............ A61N 1/36157 607/2 |
| 7,890,176 B2 | 2/2011 | Jaax et al. |
| 7,933,654 B2 | 4/2011 | Merfeld et al. |
| 7,937,145 B2 | 5/2011 | Dobak |
| 8,010,198 B2 | 8/2011 | Libbus et al. |
| 8,027,718 B2 | 9/2011 | Spinner et al. |
| 8,046,075 B2 | 10/2011 | Rezai |
| 8,060,208 B2 | 11/2011 | Kilgore et al. |
| 8,082,038 B2 | 12/2011 | Simon et al. |
| 8,082,039 B2 | 12/2011 | Kim et al. |
| 8,170,675 B2 | 5/2012 | Alataris et al. |
| 8,209,021 B2 | 6/2012 | Alataris et al. |
| 8,209,028 B2 | 6/2012 | Skelton et al. |
| 8,224,453 B2 | 7/2012 | De Ridder |
| 8,255,057 B2 | 8/2012 | Fang et al. |
| 8,280,515 B2 | 10/2012 | Greenspan |
| 8,355,792 B2 | 1/2013 | Alataris et al. |
| 8,355,797 B2 | 1/2013 | Caparso |
| 8,359,102 B2 | 1/2013 | Alataris et al. |
| 8,359,103 B2 | 1/2013 | Alataris et al. |
| 8,380,318 B2 | 2/2013 | Kishawi et al. |
| 8,396,559 B2 | 3/2013 | Alataris et al. |
| 8,423,147 B2 | 4/2013 | Alataris et al. |
| 8,428,748 B2 | 4/2013 | Alataris et al. |
| 8,509,905 B2 | 8/2013 | Alataris et al. |
| 8,554,326 B2 | 10/2013 | Alataris et al. |
| 8,694,109 B2 | 4/2014 | Alataris et al. |
| 8,712,533 B2 | 4/2014 | Alataris et al. |
| 8,712,534 B2 | 4/2014 | Wei |
| 8,718,781 B2 | 5/2014 | Alataris et al. |
| 8,718,782 B2 | 5/2014 | Alataris et al. |
| 8,768,472 B2 | 7/2014 | Fang et al. |
| 8,774,926 B2 | 7/2014 | Alataris et al. |
| 8,874,217 B2 | 10/2014 | Alataris et al. |
| 8,874,221 B2 | 10/2014 | Alataris et al. |
| 9,220,889 B2 | 12/2015 | Carlton et al. |
| 9,278,215 B2 | 3/2016 | Thacker et al. |
| 9,283,387 B2 | 3/2016 | Thacker et al. |
| 9,283,388 B2 | 3/2016 | Thacker et al. |
| 9,789,313 B2 * | 10/2017 | Lipani .................. A61B 18/20 |
| 10,799,701 B2 | 10/2020 | Lee |
| 2002/0055779 A1 | 5/2002 | Andrews |
| 2002/0128700 A1 | 9/2002 | Cross |
| 2003/0120323 A1 | 6/2003 | Meadows et al. |
| 2003/0204221 A1 | 10/2003 | Rodriguez et al. |
| 2003/0236558 A1 * | 12/2003 | Whitehurst ........ A61N 1/36071 607/45 |
| 2004/0015202 A1 | 1/2004 | Chandler et al. |
| 2004/0034394 A1 | 2/2004 | Woods et al. |
| 2004/0039425 A1 | 2/2004 | Greenwood-Van Meerveld |
| 2004/0073273 A1 | 4/2004 | Gluckman et al. |
| 2004/0162590 A1 | 8/2004 | Whitehurst et al. |
| 2004/0167584 A1 | 8/2004 | Carroll et al. |
| 2004/0210270 A1 | 10/2004 | Erickson |
| 2005/0033381 A1 | 2/2005 | Carter et al. |
| 2005/0038489 A1 | 2/2005 | Grill |
| 2005/0060001 A1 | 3/2005 | Singhal et al. |
| 2005/0113882 A1 | 5/2005 | Cameron et al. |
| 2005/0119713 A1 | 6/2005 | Whitehurst et al. |
| 2005/0143789 A1 | 6/2005 | Whitehurst et al. |
| 2005/0153885 A1 | 7/2005 | Yun et al. |
| 2005/0246006 A1 | 11/2005 | Daniels |
| 2006/0004422 A1 | 1/2006 | De Ridder |
| 2006/0041285 A1 | 2/2006 | Johnson |
| 2006/0074456 A1 | 4/2006 | Pyles et al. |
| 2006/0095088 A1 | 5/2006 | De Ridder |

(56) References Cited

U.S. PATENT DOCUMENTS

| | | |
|---|---|---|
| 2006/0100671 A1 | 5/2006 | Ridder |
| 2006/0161219 A1 | 7/2006 | Mock et al. |
| 2006/0161235 A1 | 7/2006 | King |
| 2006/0190048 A1 | 8/2006 | Gerber |
| 2006/0229687 A1 | 10/2006 | Goetz et al. |
| 2006/0253182 A1 | 11/2006 | King |
| 2007/0021803 A1 | 1/2007 | Deem et al. |
| 2007/0032827 A1 | 2/2007 | Katims |
| 2007/0039625 A1 | 2/2007 | Heruth et al. |
| 2007/0049991 A1 | 3/2007 | Klostermann et al. |
| 2007/0060954 A1 | 3/2007 | Cameron et al. |
| 2007/0066997 A1 | 3/2007 | He et al. |
| 2007/0073353 A1 | 3/2007 | Rooney et al. |
| 2007/0073354 A1 | 3/2007 | Knudson et al. |
| 2007/0106337 A1 | 5/2007 | Errico et al. |
| 2007/0150034 A1 | 6/2007 | Rooney et al. |
| 2007/0156183 A1 | 7/2007 | Rhodes |
| 2007/0179559 A1 | 8/2007 | Giftakis et al. |
| 2007/0179579 A1 | 8/2007 | Feler et al. |
| 2007/0239226 A1 | 10/2007 | Overstreet |
| 2007/0244522 A1 | 10/2007 | Overstreet |
| 2007/0299482 A1 | 12/2007 | Littlewood et al. |
| 2008/0033511 A1 | 2/2008 | Dobak |
| 2008/0103570 A1 | 5/2008 | Gerber |
| 2008/0167697 A1 | 7/2008 | Johnson |
| 2008/0183259 A1 | 7/2008 | Bly et al. |
| 2008/0234791 A1 | 9/2008 | Arle et al. |
| 2009/0036945 A1 | 2/2009 | Chancellor et al. |
| 2009/0054962 A1 | 2/2009 | Lefler et al. |
| 2009/0132010 A1 | 5/2009 | Kronberg |
| 2009/0157141 A1 | 6/2009 | Chiao et al. |
| 2009/0157149 A1 | 6/2009 | Wahlgren et al. |
| 2009/0198306 A1 | 8/2009 | Goetz et al. |
| 2009/0204173 A1 | 8/2009 | Fang et al. |
| 2009/0281595 A1 | 11/2009 | King et al. |
| 2009/0287274 A1 | 11/2009 | De Ridder |
| 2009/0326611 A1 | 12/2009 | Gillbe |
| 2010/0016929 A1 | 1/2010 | Prochazka |
| 2010/0036454 A1 | 2/2010 | Bennett et al. |
| 2010/0094375 A1 | 4/2010 | Donders et al. |
| 2010/0125313 A1 | 5/2010 | Lee et al. |
| 2010/0137938 A1 | 6/2010 | Kishawi et al. |
| 2010/0191307 A1 | 7/2010 | Fang et al. |
| 2010/0241190 A1 | 9/2010 | Kilgore et al. |
| 2010/0274312 A1 | 10/2010 | Alataris et al. |
| 2010/0274314 A1 | 10/2010 | Alataris et al. |
| 2010/0274315 A1 | 10/2010 | Alataris et al. |
| 2010/0274316 A1 | 10/2010 | Alataris et al. |
| 2010/0274317 A1 | 10/2010 | Parker et al. |
| 2010/0274318 A1 | 10/2010 | Walker et al. |
| 2010/0274320 A1 | 10/2010 | Torgerson |
| 2010/0274326 A1 | 10/2010 | Chitre et al. |
| 2010/0324630 A1 | 12/2010 | Lee et al. |
| 2010/0331916 A1 | 12/2010 | Parramon et al. |
| 2011/0009919 A1 | 1/2011 | Carbunaru et al. |
| 2011/0009923 A1 | 1/2011 | Lee |
| 2011/0022114 A1 | 1/2011 | Navarro |
| 2011/0184486 A1 | 7/2011 | De Ridder |
| 2011/0184488 A1 | 7/2011 | De Ridder |
| 2011/0201977 A1 | 8/2011 | Tass |
| 2011/0276107 A1 | 11/2011 | Simon et al. |
| 2011/0282412 A1 | 11/2011 | Glukhovsky et al. |
| 2012/0089200 A1 | 4/2012 | Ranu et al. |
| 2012/0172946 A1 | 7/2012 | Alataris et al. |
| 2012/0277833 A1 | 11/2012 | Gerber et al. |
| 2012/0283797 A1 | 11/2012 | De Ridder |
| 2013/0006325 A1 | 1/2013 | Woods et al. |
| 2013/0023951 A1 | 1/2013 | Greenspan |
| 2013/0041425 A1 | 2/2013 | Fang et al. |
| 2013/0066411 A1 | 3/2013 | Thacker et al. |
| 2013/0116754 A1 | 5/2013 | Sharma et al. |
| 2013/0172955 A1 | 7/2013 | Alataris et al. |
| 2013/0204173 A1 | 8/2013 | Kelly et al. |
| 2013/0204323 A1 | 8/2013 | Thacker et al. |
| 2013/0211487 A1 | 8/2013 | Fang et al. |
| 2013/0282078 A1 | 10/2013 | Wacnik |
| 2014/0031896 A1 | 1/2014 | Alataris et al. |
| 2014/0276549 A1 | 9/2014 | Osorio |
| 2015/0217116 A1 | 8/2015 | Parramon et al. |
| 2016/0082252 A1 | 3/2016 | Hershey et al. |
| 2016/0175594 A1 | 6/2016 | Min et al. |
| 2017/0036023 A1 | 2/2017 | Parker |
| 2017/0165485 A1 | 6/2017 | Sullivan et al. |
| 2020/0254255 A1 | 8/2020 | Lee |

FOREIGN PATENT DOCUMENTS

| | | |
|---|---|---|
| WO | WO-02065896 A2 | 8/2002 |
| WO | WO-02092165 A1 | 11/2002 |
| WO | WO-2007082382 A1 | 7/2007 |
| WO | WO-2007117232 A1 | 10/2007 |
| WO | WO-2008039982 A2 | 4/2008 |
| WO | WO-2008045434 A2 | 4/2008 |
| WO | WO-2008121891 A1 | 10/2008 |
| WO | WO-2011014570 A1 | 2/2011 |
| WO | WO-2013116368 A1 | 8/2013 |

OTHER PUBLICATIONS

Barolat et al., "Multifactorial Analysis of Epidural Spinal Cord Stimulation,"Sterotactic and Functional Neurosurgery, 1991; 56: 77-103.

Bhadra et al., "High Frequency electrical conduction block of the pudendal nerve," Journal of Neural Engineering—Institute of Physics Publishing, 2006, 8 pages.

Bhadra et al., Stimulation of High-Frequency Sinusoidal Electrical Block of Mammalian Myelinated Axons, J Comput Neurosco, 22:313-326, 2007.

Bhadra MD, Niloy et al., "High-Frequency Electrical Conduction Block of Mammalian Peripheral Motor Nerve," Muscle and Nerve, Dec. 2005, 9 pages.

Boger et al., "Bladder Voiding by Combined High Frequency Electrical Pudendal Nerve Block and Sacral Root Stimulation," Neurourology and Urodynamics, 27, 2008, 5 pages.

Bowman and McNeal, Response of Single Alpha Motoneurons to High-Frequency Pulse Trains, Appl. Neurophysiol. 49, p. 121-138, 1986, 10 pages.

Burton, Charles, "Dorsal Column Stimulation: Optimization of Application," Surgical Neurology, vol. 4, No. 1, Jul. 1975, 10 pages.

Cuellar et al., "Effect of High Frequency Alternating Current on Spinal Afferent Nociceptive Transmission," Neuromodulation: Technology at the Neural Interface, 2012, 10 pages.

DeRidder et al., "Are Paresthesias necessary for pain suppression in SCS—Burst Stimulation," Brain, Brain Research Center Antwerp of Innovative and Interdisciplinary Neuromodulation, 2010, 27 pages.

DeRidder et al., "Burst Spinal Cord Stimulation: Toward Paresthesia-Free Pain Suppression," www.neurosurgery-online.com, vol. 66, Nos. 5, May 2010, 5 pages.

Grill, Warren et al., "Stimulus Waveforms for Selective Neural Stimulation," IEEE Engineering in Medicine and Biology, Jul./Aug. 1995, pp. 375-385.

Holsheimer—Effectiveness of Spinal Cord Stimulation in the Management of Chronic Pain: Analysis of Technical Drawbacks and Solutions, Neurosurgery, vol. 40, No. 5, May 1997, pp. 990-999.

Hopp et al., "Effect of anodal blockade of myelinated fibers on vagal c-fiber afferents," American Journal Physiological Society, Nov. 1980; 239(5), 9 pages.

Hoppenstein, Reuben, "Electrical Stimulation of the Ventral and Dorsal Columns of the Spinal Cord for Relief of Chronic Intractable Pain: Preliminary Report," Surgical Neurology, vol. 4, No. 1, Jul. 1975, 9 pages.

Huxely et al., "Excitation and Conduction in Nerve: Quantitative Analysis," Science, Sep. 11, 1964; 145: 1154-9.

Jang et al., "Analysis of Failed Spinal Cord Stimulation Trails in the Treatment of Intractable Chronic Pain," J. Korean Neurosurg Soc 43, 2008, 5 pages.

(56) References Cited

OTHER PUBLICATIONS

Kilgore et al. "Nerve Conduction Block Utilizing High-Frequency Alternating Current" Medical & Biology Engineering and Computing, 2004, vol. 42, pp. 394-406.
Kilgore et al. "Nerve Conduction Block Utilizing High-Frequency Alternating Current" Medical & Biology Engineering and Computing, 2004, vol. 24, pp. 394-406.
Kilgore et al. "Reversible Nerve Conduction Block Using Kilohertz Frequency Alternating Current," Neuromodulation Technology at the Neural Interface, International Neuromodulation Society, 2013, 13 pages.
Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.
Lachance et al., "Stimulation-induced ectopicity and propagation windows in model damaged axons," J. Comput Neurosci, 2014, 9 pages.
Linderoth et al., "Mechanisms of Spinal Cord Stimulation in Painful Syndromes: Role of Animal Models," Pain Medicine, vol. 7, No. S1, 2006, 13 pages.
Linderoth et al., "Physiology of Spinal Cord Stimulation: Review and Update," Neuromodulation, vol. 2, No. 3, 1999, 15 pages.
Mediati, R.D., , "Mechanisms of Spinal Cord Stimulation," Florence, Oct. 2, 2002, 31 pages.
Melzack, Ronald et al., "Pain Mechanisms: A New Theory," Science, vol. 150, No. 3699, Nov. 19, 1965, 9 pages.
Muller and Hunsperger, "Helvetica Physiologica Acta—Reversible Blockierung der Erregungsleitung im Nerven durch Mittelfrequenz-Daverstrom," Schwabe & Co. Basel, vol. 25, Fasc. 1, 1967, 4 pages.
North et al., "Failed Back Surgery Syndrome: 5-year Follow-Up after Spinal Cord Stimulator Implantation," Neurosurgery, Official Journal of the Congress of Neurological Surgeons, vol. 28, No. 5, May 1991, 9 pages.
North et al., "Spinal Cord Stimulation for Axial Low Back Pain," Spine, vol. 30, No. 12, 2005, 7 pages.
North et al., "Spinal Cord Stimulation for Chronic, Intractable Pain: Experience over Two Decades," Neurosurgery, vol. 32, No. 2, Mar. 1993, 12 pages.
Oakley, John C., "Spinal Cord Stimulation Mechanisms of Action," Spine vol. 27, No. 22, copyright 2002, 10 pages.
Perruchoud et al., "Analgesic Efficacy of High-Frequency Spinal Cord Stimulation: A Randomized Double-Blind Placebo-Controlled Study," Neuromodulation: Technology at Neural Interface, International Neuromodulation Society, 2013, 7 pages.
Shealy MD, C. Norman et al., "Electrical Inhibition of Pain by Stimulation of the Dorsal Columns: Preliminary Clinical Report," Anesthesia and Analgesia . . . Current Researches, vol. 446, No. 4, Jul.-Aug. 1967, 3 pages.

Simpson, BA, "Spinal Cord Stimulation in 60 cases of Intractable Pain." Journal of Neurology, Neurosurgery and Psychiatry, 1991; 54 pp. 196-199.
Simpson, BA, "Spinal Cord Stimulation." British Journal of Neurosurgery, Feb. 11, 1997 (1), 5-11, 7 pages.
Solomonow et al., "Control of Muscle Contractile Force through Indirect High-Frequency Stimulation," AM Journal of Physical Medicine, 1983, vol. 62, No. 3, pp. 71-82.
Tanner, J.A., "Reversible blocking of nerve conduction by alternating-current excitation," Nature, Aug. 18, 1962; 195: 712-3.
Tiede et al., "Novel Spinal Cord Stimulation Parameters in Patients with Predominate Back Pain," Neuromodulation: Technology at the Neural Interface, 2013, 6 pages.
Urban et al., "Percutaneous epidural stimulation of the spinal cord for relief of pain—Long Term Results," Journal of Neurosurgery, vol. 48, Mar. 1978, 7 pages.
Van Butyen et al., "High Frequency Spinal Cord Stimulation for the Treatment of Chronic Back Pain Patients: Results of a Prospective Multicenter European Clinical Study," Neuromodulation Technology at the Neural Interface, International Neuromodulation Society, 2012, 8 pages.
Van Den Honert et al. "Generation of Unidirectionally Propagated Action Potentials Nerve by Brief Stimuli" Science, vol. 26, pp. 1311-1312.
Van Den Honert, Mortimer JT, "A Technique for Collision Block of Peripheral Nerve: Frequency Dependence," MP-11 IEEE Trans. Biomed, Eng. 28: 379-382, 1981.
Wallin et al., "Spinal Cord Stimulation inhibits long-term potentiation of spinal wide dynamic range neurons," Elsevier Science B.V., Brain Research, 5 pages 2003.
Wolter et al., "Continuous Versus Intermittent Spinal Cord Stimulation: An Analysis of Factors Influencing Clinical Efficacy," Neuromodulation: Technology at Neural Interface, www.neuromodulationjournal.com, 2011, 8 pages.
Woo MY, Campbell B. "Asynchronous Firing and Block of Peripheral Nerve Conduction by 20KC Alternating Current," Los Angeles Neuro Society, Jun. 1964; 87-94, 5 pages.
Zhang et al., "Simulation Analysis of Conduction Block in Myelinated Axons Induced by High-Frequency Biphasic Rectangular Pulses," IEEE Transactions on Biomedical Engineering, vol. 53., No. 7, Jul. 2006, 4 pages.
Zhu et al., "Changes in functional properties of A-type but not C-type sensory neurons in vivo in a rat model of peripheral neuropathy," Journal of Pain Research, Dovepress, 2012, 18 pages.
Zhu et al., "Early Demyelination of Primary A-Fibers Induces a Rapid-Onset of Neuropathic Pain in Rat," Neuroscience 200, 2012, 13 pages.
Zhu et al., "Excitability of Aβ sensory neurons is altered in an animal model of peripheral neuropathy," BMC Neuroscience, 13:15, 2012, 15 pages.

* cited by examiner

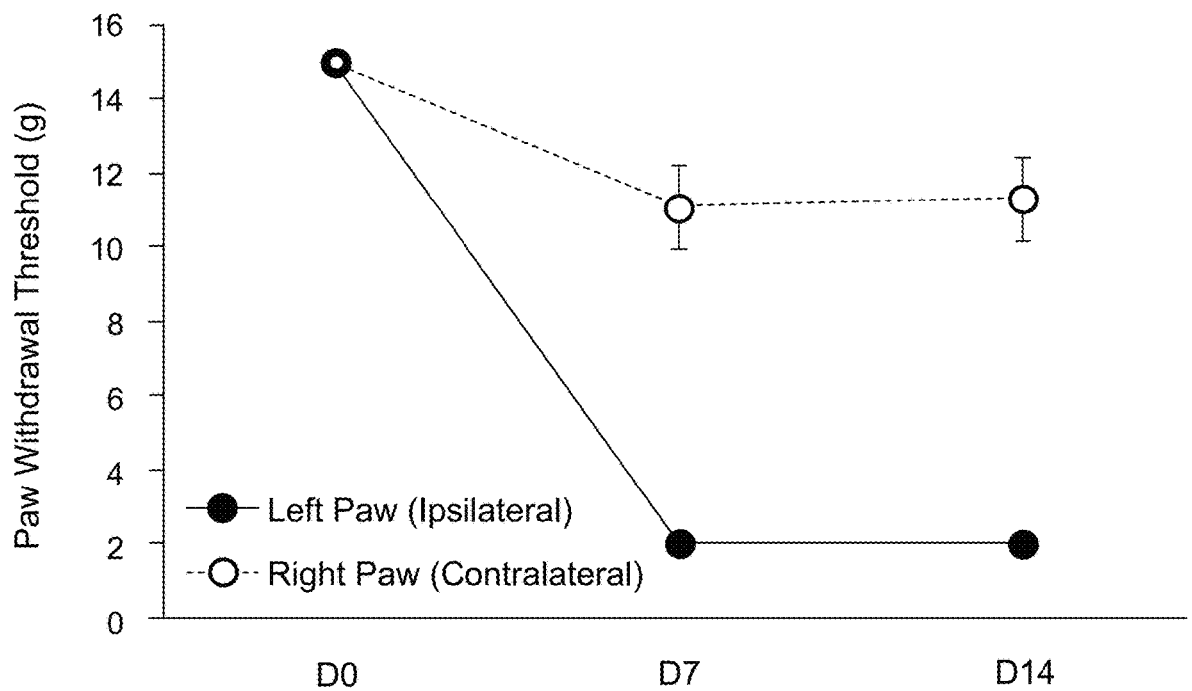
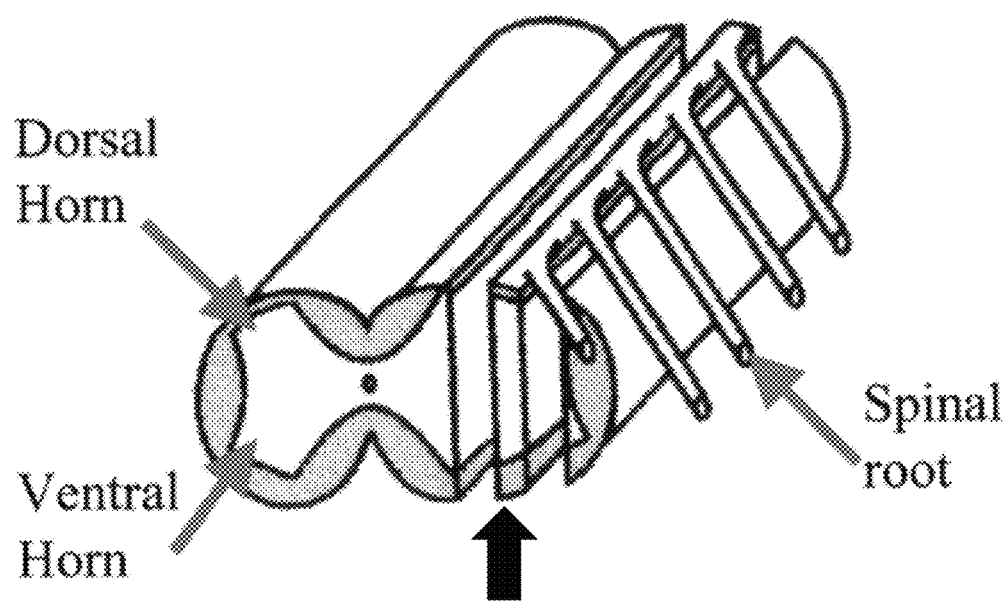
FIG. 2

Morphology of spinal cord dorsal horn neuron

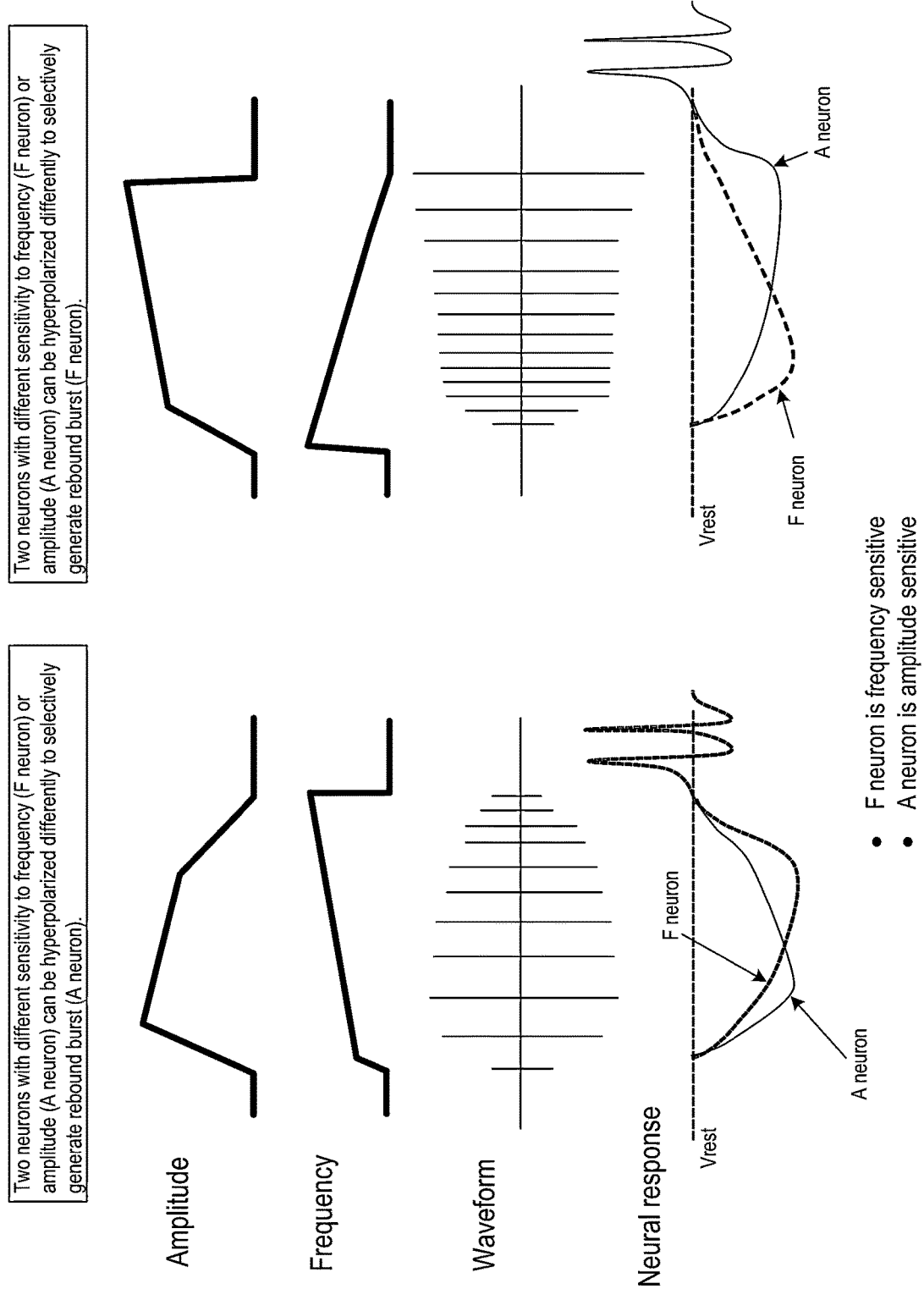

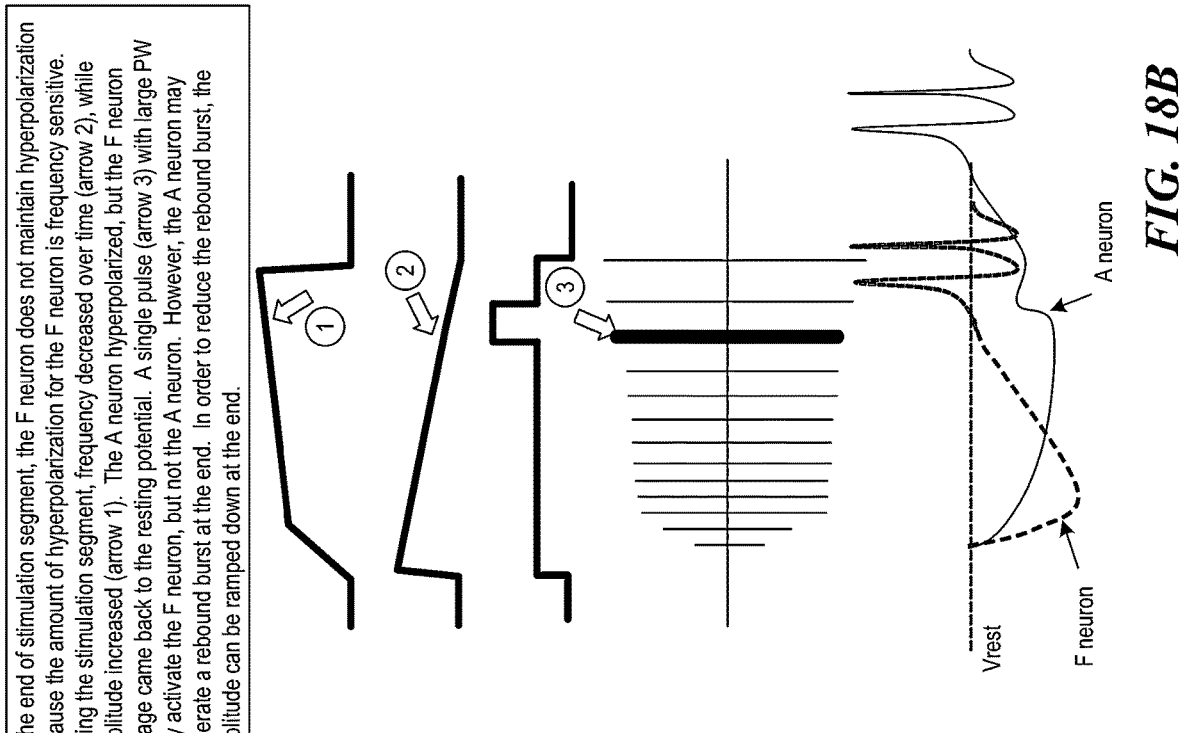
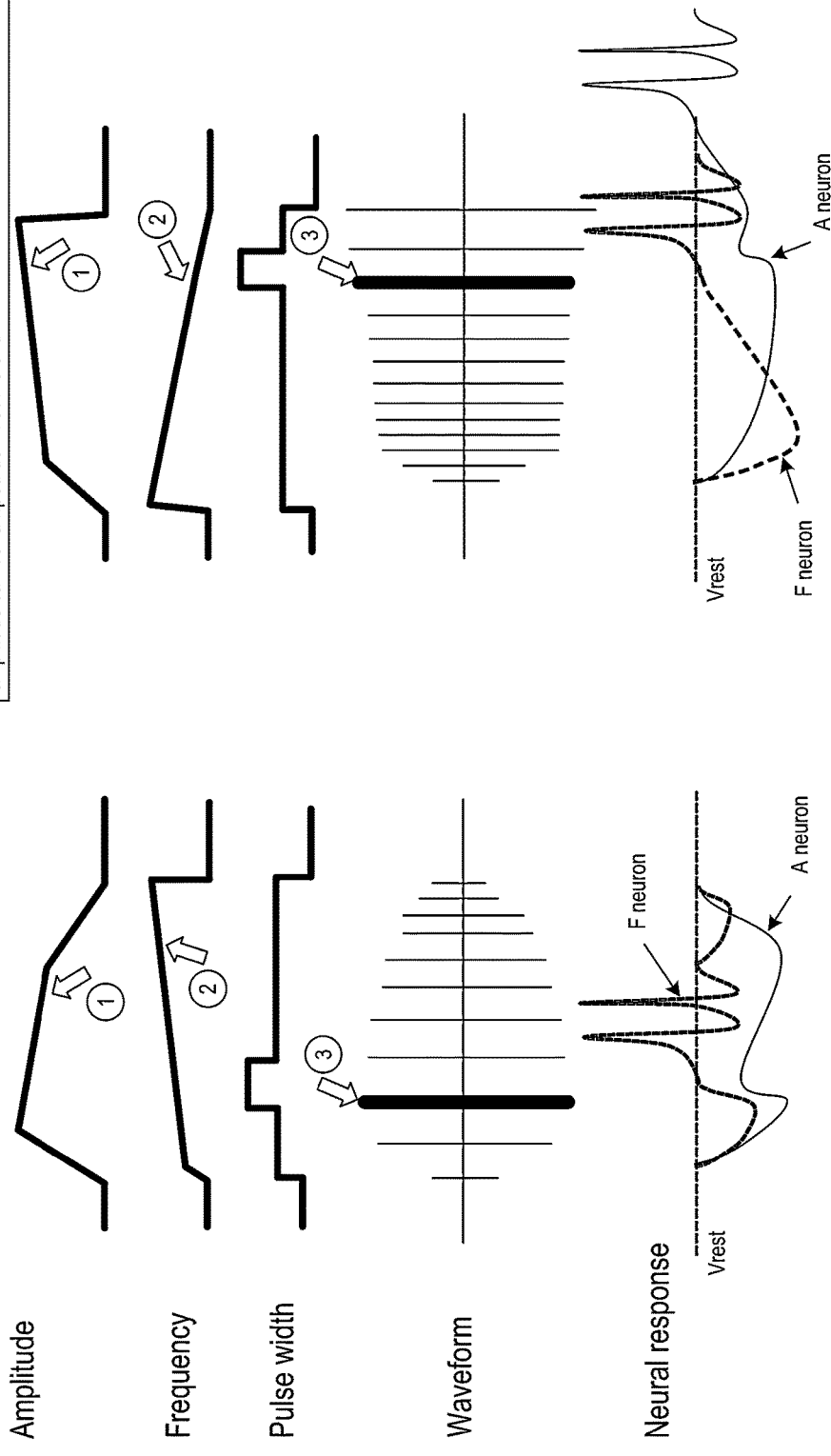
FIG. 18A
FIG. 18B

HIGH FREQUENCY ELECTROMAGNETIC STIMULATION FOR MODULATING CELLS, INCLUDING SPONTANEOUSLY ACTIVE AND QUIESCENT CELLS, AND ASSOCIATED SYSTEMS AND METHODS

CROSS-REFERENCE TO RELATED APPLICATION

The present application claims priority to U.S. Provisional Application No. 62/342,855, filed on May 27, 2016, and incorporated herein by reference in its entirety

TECHNICAL FIELD

The present disclosure is directed generally to high frequency electromagnetic stimulation for modulating cells, including spontaneously active and quiescent cells, and associated systems and methods.

BACKGROUND

The plasma membrane of a cell is responsible for maintaining the cell's resting membrane potential. The resting membrane potential is the voltage difference between the cell's extracellular space and intracellular space when the cell is in a resting state (e.g., not receiving any external stimuli). For example, the average resting membrane potential for a typical neuron is about −70 mV (with the intracellular fluid more negative than the extracellular fluid) and enables the neuron to generate electrical signals. A neuron's ability to generate and propagate an electrical signal is critical to the transfer of information within the nervous system. Neuronal signaling, for example, typically occurs via the following pathway: (1) a neuron, in a resting state, receives a physical, electrical, electromagnetic, acoustic or chemical signal at the membrane; (2) the electrical, chemical, or physical signal opens a particular type of positive ion (cation) channel spanning the membrane (e.g., channels specific to sodium ions), thereby allowing an influx of specific positive ions (e.g., $Na^+$, $Ca^{++}$) into the intracellular space; (3) the influx of these particular positive ions depolarizes (makes less negative) the intracellular space at the membrane near the affected ion channel; (4) the local depolarization causes nearby voltage-gated, positive ion channels to open, thereby further depolarizing the local intracellular space; (5) once the localized depolarization reaches a membrane potential value more positive than a certain membrane potential threshold, the depolarization process is driven by a rapid positive feedback loop (e.g., depolarization opens more voltage-gated channels, which causes more depolarization, which opens more voltage-gated channels, etc.) resulting in an action potential that propagates along the membrane. These ionic fluctuations in the membrane essentially create an electrical current flow in the neuron. When the current reaches the axon terminal of the neuron, neurotransmitters are released to the adjacent neurons, thereby chemically transmitting the signal.

The magnitude of the resting membrane potential greatly affects the neuron's ability to generate an action potential, and thus greatly affects the neuron's ability to effectively communicate with other neurons. The magnitude of the neuron's membrane potential depends on many factors, including but not limited to, whether the neuron is spontaneously active or quiescent. In some parts of the body, spontaneous activity of neurons is appropriate, normal behavior (e.g., in the sinus and AV nodes of the heart, where spontaneous depolarization provides regular automatic cell firing to drive the cardiac cycle). However, in other neural systems, spontaneous activity of certain neurons is dysfunctional (e.g., ectopic foci in epileptic conditions). Spontaneously active neurons can also be found proximal to damaged, diseased or otherwise abnormal or unhealthy tissue, as chemical mediators from those tissues can trigger changes in what were previously quiescent neurons. Contrary to quiescent neurons, which generally have an average resting potential and are functioning normally (e.g., do not spontaneously generate an action potential), the membrane potential of spontaneously active neurons is difficult to predict as these neurons are typically dysfunctional and generate a pathological action potential absent a physical, electrical, electromagnetic, acoustic or chemical signal. While applying an electrical signal to a neuron triggers an action potential, the difference in membrane potentials between spontaneously active and quiescent neurons can render the appropriate electrical stimulation needed to stimulate each type of neuron difficult to predict.

At present, a number of diseases are either known or thought to arise from spontaneously firing active neurons, or to be propagated by quiescent neurons. The difficulty in treating such diseases may be due to the difficulty in electrically modifying spontaneously active neurons (e.g., because the appropriate electrical parameters are unknown), or may be due a need to modify other neurons, such as quiescent neurons, using certain electrical parameters. Accordingly, there is a need for systems and methods for treating diseases that create dysfunctional spontaneously active neurons and/or quiescent neurons that propagate dysfunctional signaling.

BRIEF DESCRIPTION OF THE DRAWINGS

FIG. 2 is a chart comparing paw withdrawal thresholds of rats following spinal nerve ligation, obtained prior to an in vitro study in accordance with the present technology, and a diagram illustrating the location in the spinal cord from which the longitudinal slices were obtained.

FIGS. 17A and 17B illustrate the effects of amplitude- and frequency-modulated waveforms on the neural response of neurons that are frequency and amplitude sensitive, in accordance with embodiments of the present technology.

FIGS. 18A and 18B illustrate the effects of amplitude modulation, frequency modulation, and pulse width modulation on neurons that are frequency-sensitive and amplitude-sensitive, in accordance with embodiments of the present technology.

DETAILED DESCRIPTION 1.0 Introduction

Figure 1:
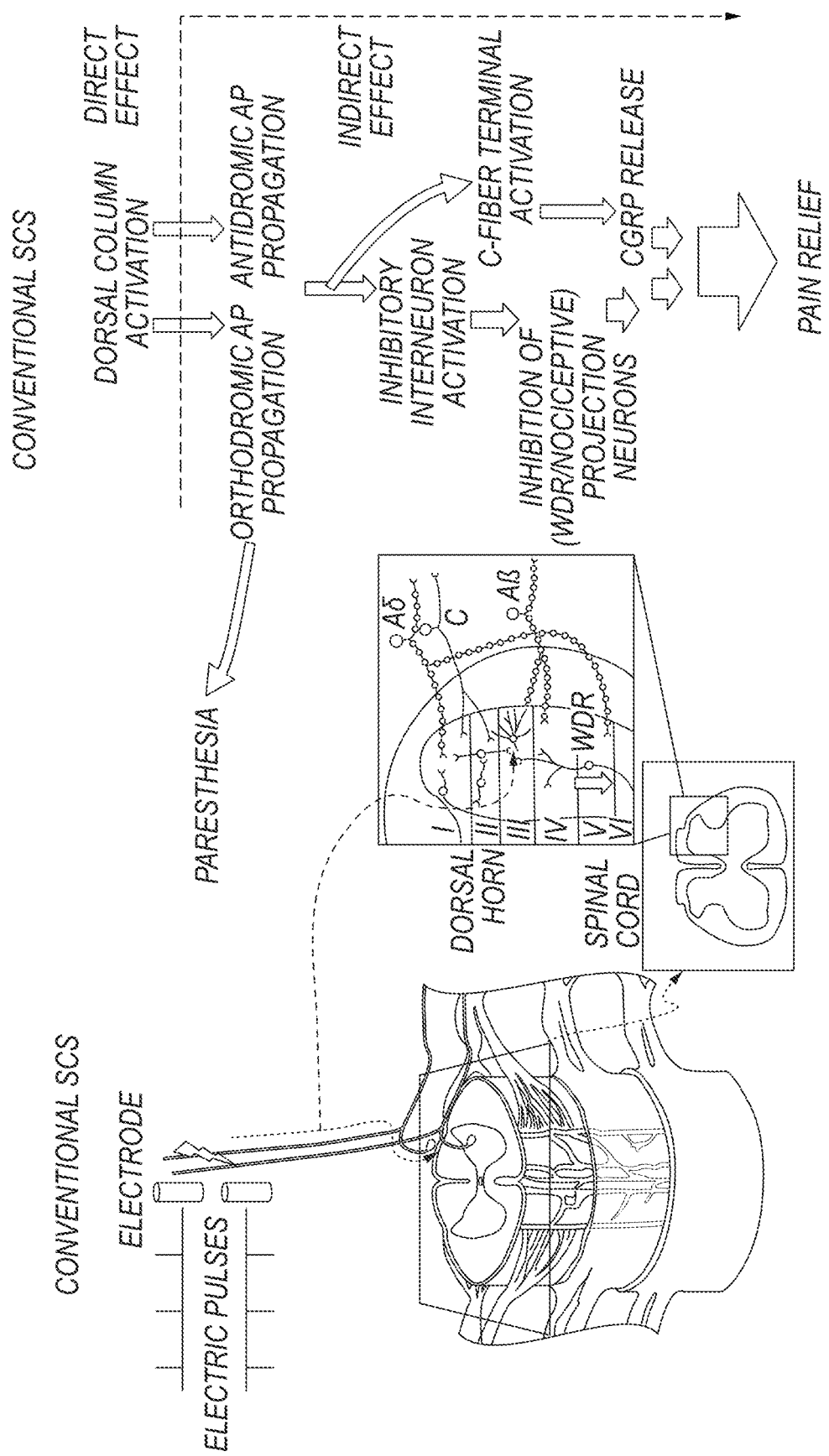
FIG. 1 is a diagram illustrating conventional SCS methods and associated pathways, based generally on information from Linderoth and Foreman (2006) and Wu et al (2007).

The present technology is directed generally to systems and methods for treating or slowing the progression of one or more diseases, and/or symptoms associated with one or more diseases. In one embodiment, the present technology includes a treatment system having a signal generator and a signal delivery element configured to apply an electromagnetic signal (e.g., an electrical signal, or another type of electromagnetic signal) to target tissue at the brain, spinal cord and/or other target areas such as peripheral nerves, the vagal nerve, mixed nerves (e.g., the pudendal nerve), autonomic ganglia, and/or sympathetic chain. In some embodiments, the electrical signal can be a high frequency signal configured to directly affect constituents of the cellular membrane to restore the signaling capabilities of the cells to normal homeostatic behavior. In some embodiments, the cells are neurons and in other embodiments, the cells are any neurologic cells, such as glial cells. In still further embodiments, the cells are non-neurologic cells. In some embodiments, the signal delivery element is configured to apply a high frequency electrical signal specifically directed at tissues within the brain and/or the spinal cord to deactivate overactive glial cells in the white matter. In other embodiments, the signal delivery element is configured to apply a high frequency electrical signal specifically directed to the vagal nerve, sacral roots, autonomic ganglia, and/or sympathetic chain to deactivate overactive neurons, stimulate underactive neurons, inhibit disease-transmission neurons, or stimulate inactive neurons in the nervous tissue. In some embodiments, prior to application of the electrical signal, one or more locations of quiescent or spontaneously active neurons can be identified to guide the practitioner in positioning the signal delivery element, and/or selecting the parameters of treatment (e.g., amplitude, pulse width, frequency, duty cycle, etc.). For example, the practitioner can use an anatomical approach based on medical images (e.g., x-ray, CT, MRI, ultrasound, electrical impedance tomography (EIT) and/or PET images). In other embodiments, the practitioner can use physiological identification, which is based on feedback from the patient or from a measured signal (e.g., EEG, evoked potential, and/or EMG). Quiescent neurons generally cannot be identified without some input to activate neurons. Accordingly, the practitioner can use any of several suitable modalities (e.g., electrical, mechanical, thermal, psychological and/or optical stimulation) on peripheral nerves or local neurons near a target area, to activate the neurons. To identify spontaneously active neurons, the practitioner can move an electrode around one or more target areas while monitoring local neurons in real-time (e.g., via. electrode placement during a deep brain stimulation (DBS) procedure).

In other embodiments, the cells are cardiac cells and the signal delivery element is configured to apply a high frequency electrical signal specifically directed to the heart to deactivate overactive cardiac cells, stimulate underactive cardiac cells, inhibit disease-transmission cardiac cells, or stimulate inactive cardiac cells. In these embodiments, the cardiac cells may be cardiomyocytes, Purkinje fibers, and/or other cell types located in the heart. Further, in these embodiments, the cells can be cells of structures connected to the heart, such as smooth muscle cells, epithelial cells, endothelial cells, neurons, and/or others. In some embodiments, prior to application of the electrical signal, one or more locations of quiescent or spontaneously active cardiomyocytes can be identified to guide the practitioner in positioning the signal delivery element and/or selecting the parameters of treatment (e.g., amplitude, pulse width, frequency, duty cycle, etc.).

In other embodiments, the cells are gastrointestinal cells (e.g., epithelial cells or smooth muscle cells of the stomach, intestine or colon), bladder cells, skeletal muscle cells, or skin cells. The signal delivery element is configured to apply a high frequency electrical signal specifically directed to gastrointestinal, bladder, skeletal muscle or skin to deactivate the overactive cells, stimulate underactive cells, inhibit disease-transmission cells, or stimulate inactive cells in the tissue. In some embodiments, prior to application of the electrical signal, one or more locations of quiescent or spontaneously active cells can be identified to guide the practitioner in positioning the signal delivery element and/or selecting the parameters of treatment (e.g., amplitude, pulse width, frequency, duty cycle, etc.).

Many of the examples disclosed herein include applications of the present technology to neurons. Other embodiments of the present technology include application to cells other than neurons. Particular embodiments are accordingly applicable to any suitable depolarized cell, including a stem cell, certain cardiac cells, and/or other cell types treatable by energy delivery.

Several of the following embodiments can produce a therapeutic effect that includes pain reduction in the patient, e.g., in addition to treating or reducing symptoms of a disease. The therapeutic effect can be produced by inhibiting, suppressing, downregulating, blocking, preventing, and/or otherwise modulating the activity of the affected neural population. In many embodiments of the presently disclosed techniques, therapy-induced paresthesia is not a prerequisite to achieving pain reduction, unlike the conventional spinal cord stimulation (SCS) techniques described below with reference to FIG. 1. It is expected that the techniques described below with reference to FIGS. 2-23 can produce more effective, more robust, less complicated and/or otherwise more desirable results than conventional SCS therapies.

Neurological stimulators have been developed to treat pain, movement disorders, functional disorders, spasticity, cardiac disorders, and various other medical conditions. Implantable neurological stimulation systems generally have an implantable pulse generator and one or more leads or other signal delivery devices that deliver electrical pulses to neurological tissue or muscle tissue. For example, several neurological stimulation systems for SCS have cylindrical leads that include a lead body with a circular cross-sectional shape and one or more conductive rings spaced apart from each other at the distal end of the lead body. The conductive rings operate as individual electrodes and, in many cases, the SCS leads are implanted percutaneously through a large needle inserted into the epidural space, with or without the assistance of a stylet.

Once implanted, the pulse generator applies electrical pulses to the electrodes, which in turn modify the function of the patient's nervous system, such as by altering the patient's responsiveness to sensory stimuli, altering the patient's motor-circuit output, and/or otherwise modifying one or more other neural functions. Example neuromodulation systems, methods, and therapy parameters are described in the following co-owned published patent applications: US Patent Publication No. 2009/0204173; US Patent Publication No. 2010/0191307; US Patent Publication No. 2010/0274312; US Patent Publication No. 2010/0274314; US Patent Publication No. 2012/0172946; US Patent Publication No. 2013/0066411, which are all incorporated herein by reference in their entireties.

Several embodiments of neuromodulation systems, methods, and therapies for the treatment of medical conditions are described herein. The specific embodiments discussed are not to be construed as limitations on the scope of the disclosed technology. It will be apparent to one skilled in the art that various equivalents, changes, and modifications may be made without departing from the scope of the disclosed technology, and it is understood that the present disclosure encompasses such equivalent embodiments.

The following abbreviations are used herein: AIC, anterior limb internal capsule; BST, bed nucleus of the stria terminals; CMPF, centromedian and parafascicularis; DREZ, dorsal root entry zone; GF, genitofemoral; GNI, glial neuronal cell interaction; GPI, globus pallidus internus; MCS, motor cortex stimulation; MD, movement disorder; MI, primary motor cortex; ONS, occipital nerve stimulation; NAcc, nucleus accumbens; NTS, nucleus tractus solitarii; PVG, periventricular grey matter; PAG, periaqueductal grey matter; PPN, pedunculopontine nucleus; SCA, superior cerebellar artery; SCS, spinal cord stimulation; SMA, supplementary motor area; SPG, sphenopalatine ganglion; STN, subthalamic nucleus; Vcpc, ventro caudalis parvocellularis; VIP, ventral intermedia nucleus; VOA, ventralis oralis anterior; VOP, ventralis oralis posterior; VPL, ventral posterolateral nucleus; VPM, ventral posteromedial nucleus; WDR, wide dynamic range; ZI, zona incerta.

Specific details of certain embodiments of the technology are described below with reference to methods for delivering energy to one or more target neural populations or other sites of a patient, and associated implantable structures for providing the stimulation. Although selected embodiments are described below with reference to stimulating the dorsal column, dorsal horn, dorsal root, dorsal root entry zone, and/or other particular regions of the spinal column to control pain, the leads may be in some instances be used to stimulate other neurological structures of the spinal cord and/or other neurological tissues. Furthermore, other embodiments can include modulation of the myocardium (e.g., heart), gastrointestinal tissue, bladder tissue, skeletal muscle skin tissue, and/or other tissues. Some embodiments can have configurations, components or procedures different than those described in this section, and other embodiments may eliminate particular components or procedures. A person of ordinary skill in the relevant art, therefore, will understand that the disclosure may include other embodiments with additional elements, and/or may include other embodiments without several of the features shown and described below with reference to FIGS. 1-23.

As used herein, the terms "high frequency" and "HF" refer to a frequency of from about 1.5 kHz to about 100 kHz, or from about 2 kHz to about 50 kHz, or from about 3 kHz to about 20 kHz, or from about 3 kHz to about 15 kHz, or from about 5 kHz to about 15 kHz, or from about 3 kHz to about 10 kHz, or 1 kHz, 2 kHz, 3 kHz, 4 kHz, 5 kHz, 10 kHz, 15 kHz, 20 kHz, 50 kHz, or 100 kHz, unless otherwise stated. Unless otherwise stated, the term "about" refers to values within 10% of the stated value. As used herein, "low frequency" or "LF" refers to a frequency less than 1.2 kHz or less than 1 kHz.

2.0 Pertinent Neuronal Physiology and/or Pathophysiology

The following discussion provides further details regarding pertinent physiology and/or pathophysiology for the technology disclosed herein. This section is intended to provide additional context regarding the disclosed technology and the cellular effects associated with high frequency neuronal stimulation. Without being bound by theory, it is expected that techniques in accordance with the present technology can (a) inhibit spontaneously active neurons and/or increase the excitability of quiescent neurons, or (b) inhibit both spontaneously active neurons and quiescent neurons (which, by virtue of being quiescent, are already inhibited). The process by which these results occur can include deactivating or inactivating sodium channels. However, the technology disclosed herein is not limited to any particular mechanism of action, and both known and unknown mechanisms of action may be relevant to this technology, including direct effects at the cellular membrane, amongst others.

Conventional SCS (e.g., SCS at frequencies of 1200 Hz or less), causes direct and indirect effects which ultimately result in pain relief. As illustrated in FIG. 1, the direct effects include dorsal column activation. The indirect effects include orthodromic and antidromic action potential (AP) propagation, the latter of which results in inhibitory interneuron activation, and ultimately results in inhibition of wide dynamic range (pain-mediating) projection neurons. In addition, antidromic AP propagation may also activate terminal C-fibers resulting in release of calcitonin gene-related peptide (CGRP). Specific design requirements and treatment parameters may include determining alternative lead placement within a patient, type of neuron to target, the frequency of energy delivery, the pulse width, amplitude and combinations thereof.

A. Physiological and/or Pathophysiological Models

Nevro Corp., the assignee of the present application, utilized a tissue-based model and a computational model to determine the effects of high frequency electrical pulses on neurons. While not intended to be limiting or binding on the present disclosure, the results of these experiments and computational models suggest that high frequency electrical pulses directly affect one or more constituents and/or characteristics of the cellular membrane, and in particular, the electrical potentials measured at the cellular membrane. Further representative constituents include a structure of the membrane, a channel of the membrane and/or a protein of the membrane. However, such results do not exclude other explanations for the effects of high frequency electrical pulses on cells, including neurons.

i. Representative Experiments

Experiments were designed to allow for systematic recording of neural responses from rat spinal cord slices prepared from rat neuropathic pain models using SCS. The rat neuropathic pain model included ligation of the spinal nerve of adult male Sprague-Dawley rats (250-300 g in weight) in accordance with a standard procedure. (Kim and Chung, 1992.) A paw withdrawal threshold was performed as a validation study to ensure the spinal nerve was properly ligated. As shown in FIG. 2 (top), the paw withdrawal threshold for the contralateral right paw was significantly higher than the ipsilateral left paw seven days after ligation of the spinal nerve. These thresholds remained constant fourteen days after ligation. Following euthanasia, longitudinal slices comprising a portion of the dorsal horn, a portion of the ventral horn, and the attached spinal roots were prepared and maintained in artificial cerebral spinal fluid at room temperature for one hour prior to the electrophysiological (EP) recordings. A diagram of the longitudinal slice preparations is shown in FIG. 2 (bottom).

Figure 3B:
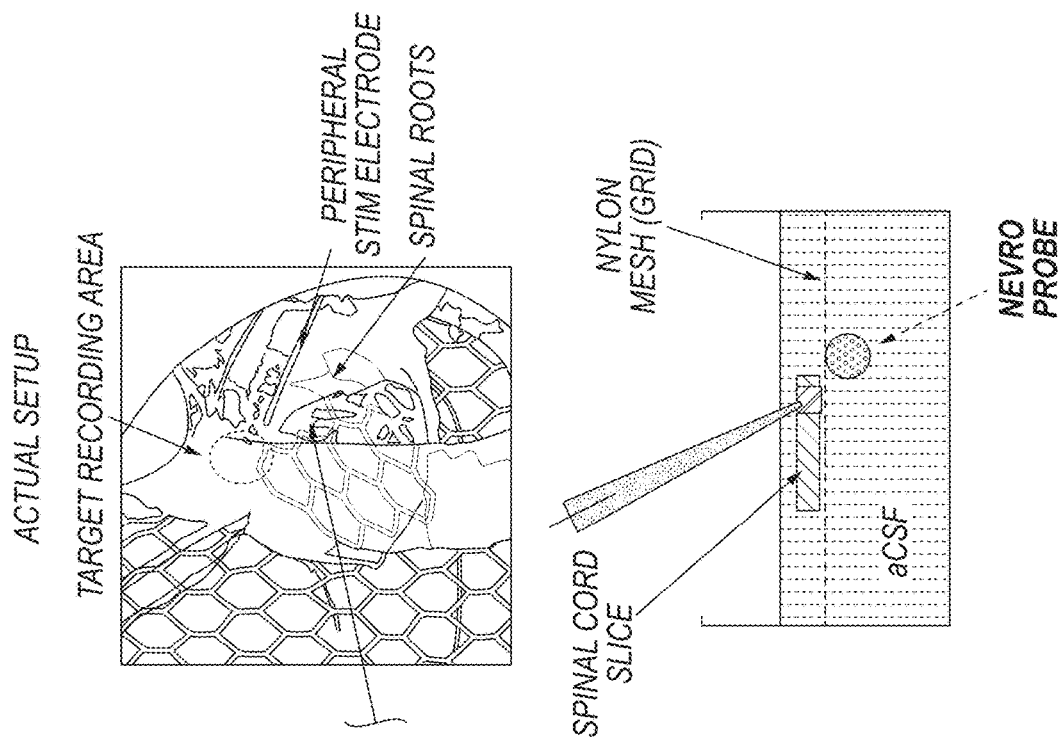
FIG. 3B is an image of electrode positioning and target recording sites for electrophysiological recordings of spinal cord slices obtained during an in vitro study in accordance with several embodiments of the present technology. A diagram illustrating a side-view of the electrode positioning and target recording sites for electrophysiological recordings is shown below the image for reference.
Figure 3A:
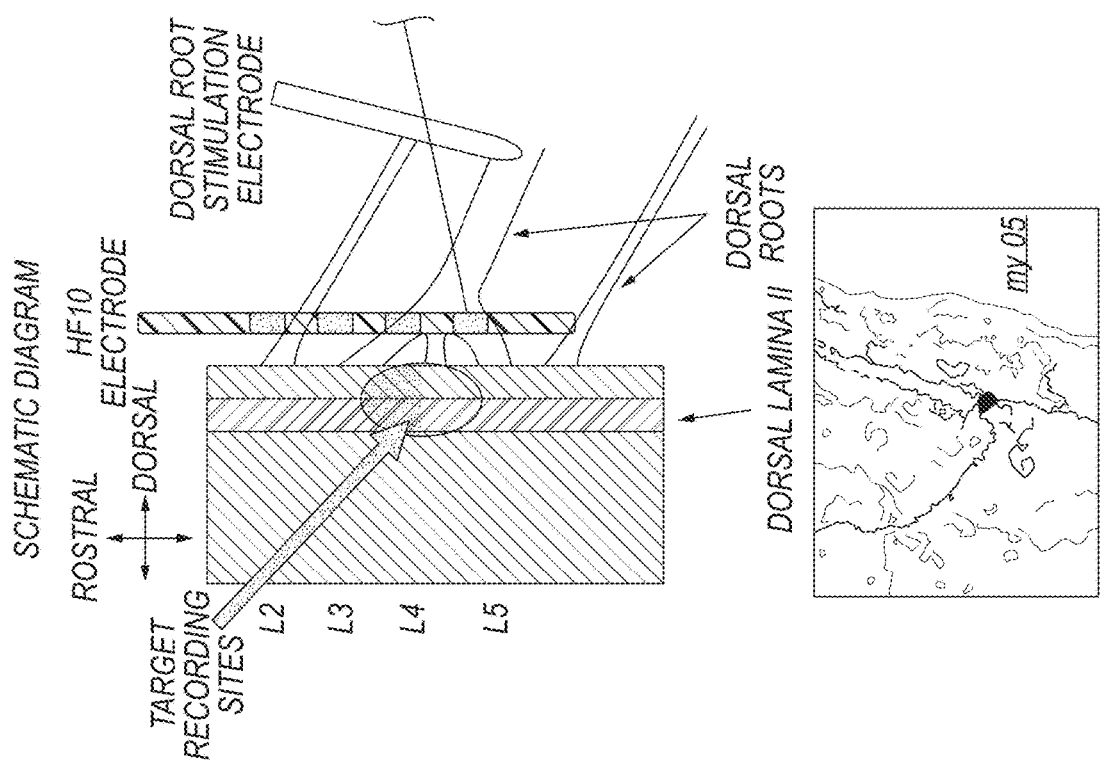
FIG. 3A is a diagram of electrode positioning and target recording sites for electrophysiological recordings of spinal cord slices obtained during an in vitro study in accordance with several embodiments of the present technology, along with an image of the dorsal lamina II, for reference.

EP recordings using a whole-cell patch clamp technique were obtained after the one hour equilibration. As show in FIG. 3A, a dorsal root stimulation electrode was placed at a dorsal root extending from the longitudinal slice. The dorsal root stimulation electrode was configured to provide a noxious stimulation by activating both small and large fibers to model different amounts of pain, including a high amount of pain, a normal amount of pain or a low amount of pain. The patch pipettes were filled with intracellular solution and the dorsal root of each slice stimulated at a pulse width of 100 µs-800 µs and a frequency of 0.1-10 Hz. As shown in FIG. 3B, a high frequency electrode was placed near the dorsal root and the dorsal lamina II to generate a (therapeutic) high frequency electrical field having a pulse width of at least 30 µs and a frequency of 1-10 kHz.

A data acquisition system (including pClamp9 software configured to record 100 Hz samples per second in a whole-patch technique) was used to record the cellular responses to electrical fields having kHz magnitudes. The recording occurred at a target recording site, or more than one target recording site, located within or near the dorsal lamina II.

ii. Representative Computational Models

Computational models were designed to reproduce the inhibition of spontaneous firing events when an equivalent current is (computationally) injected and measured during energy delivery using kHz frequencies. Using a computational model (calibrated with an experimental tissue-based model, such as the one discussed above), the direct effect of high frequency energy delivery, (or any frequency energy delivery) can be simulated. Such a simulation based on the computational model can be used to determine an amount of current sufficient to hyperpolarize a target neuron. While the computational model was further designed to model a spontaneously firing neuron, the computational model is not so limited and can be used to model another type of neuron, such as a quiescent neuron, or the like.

Figure 9A:
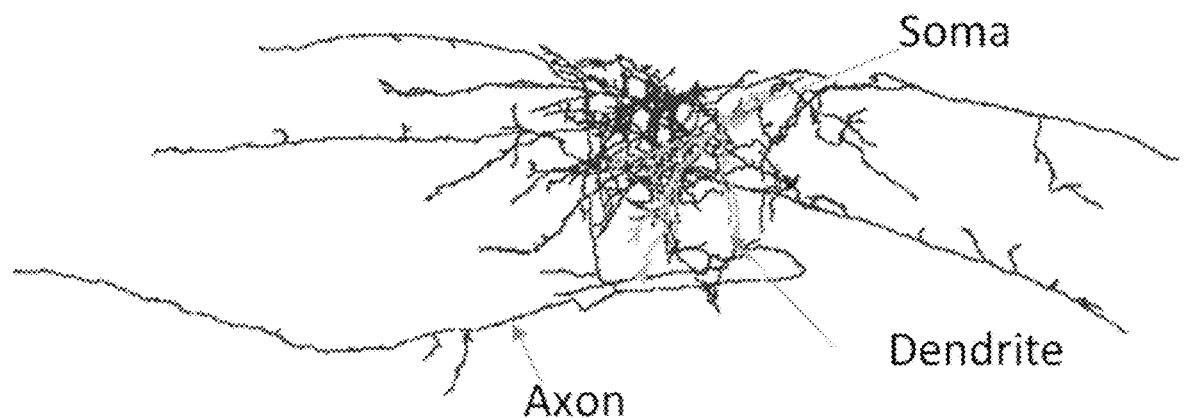
FIG. 9A is a schematic illustration of the morphology of a dorsal horn neuron located in the spinal cord, based generally on information from Szucs et al. (2013).
Figure 9B:
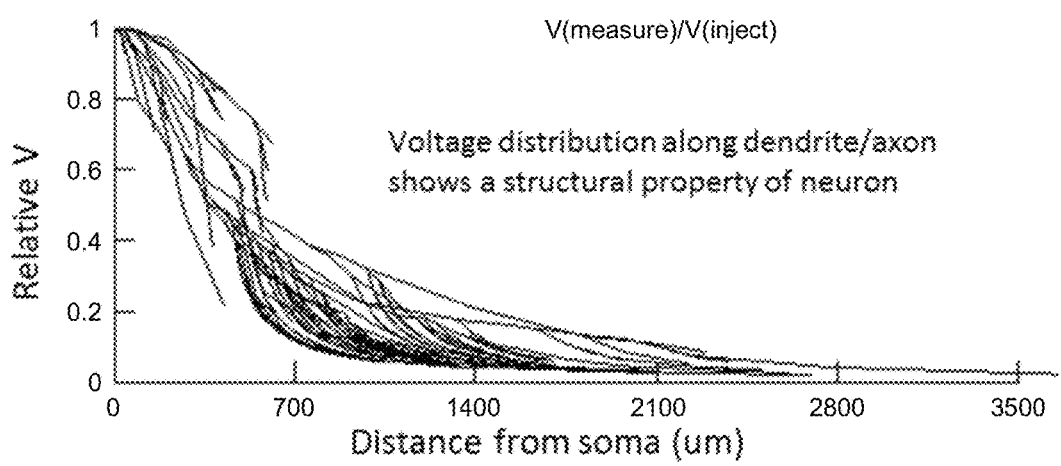
FIG. 9B is a graph illustrating the voltage distribution along a dendrite/axon of the dorsal horn neuron shown in FIG. 9A as a function of the relationship between the relative voltage and the distance from the soma.
Figure 10A:
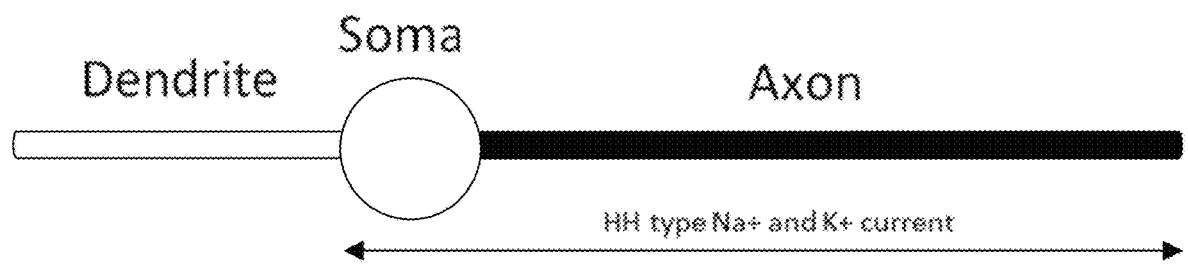
FIG. 10A is a schematic illustration of a simplified morphology, based on the morphology of a dorsal horn neuron shown in FIG. 9A.
Figure 10B:
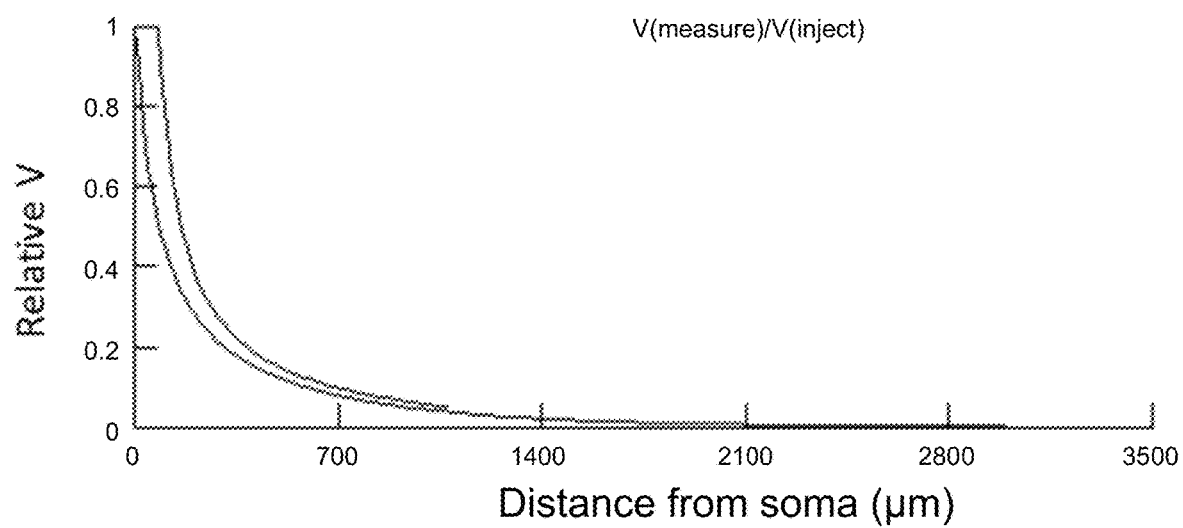
FIG. 10B is a graph illustrating the relative voltage along a simplified dendrite/axon, as depicted in FIG. 10A, as a function of the distance from the soma.

FIG. 9A illustrates the morphology of a spinal cord dorsal horn neuron, including a soma, dendrites and axons according to Szucs et al. 2013. Notably, as shown in FIG. 9B, the voltage distribution along a dendrite, and extending into the axon, decreases with increasing distance from the soma. The voltage distribution was determined as a proportion of the measured voltage ($V_{measured}$) relative to the injected voltage ($V_{injected}$). FIG. 10A is a schematic diagram simplifying the structures shown in FIG. 9A. While not intended to limit the technology described herein, FIG. 10B illustrates the measured current passing from the soma through the axon and indicates that the measured current is a Hodgkin-Huxley type $Na^+$ and $K^+$ current. The experiments and computational models described above were performed to determine responses to high frequency energy delivery in (a) quiescent neurons, and (b) spontaneously active neurons, as described below.

B. Quiescent Neurons i. Representative Experimental Data

Figure 7A:
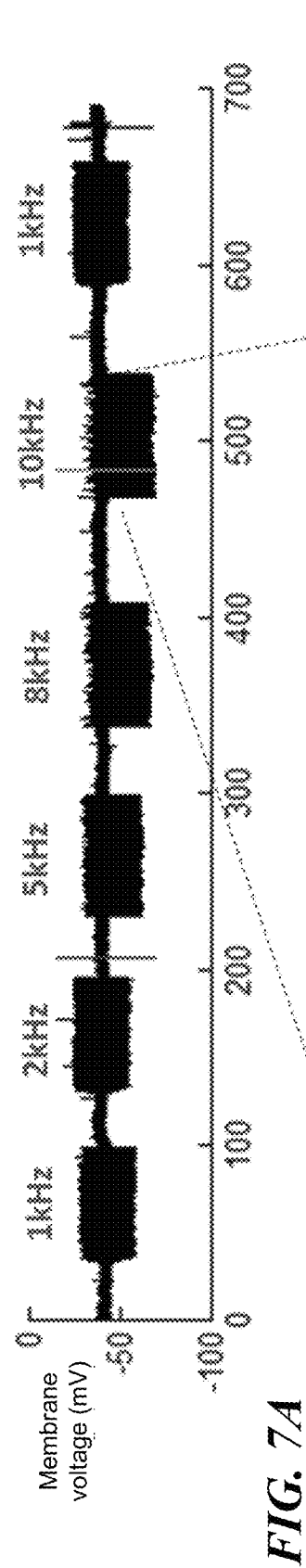
FIG. 7A is a diagram of an electrophysiological recording of a quiescent neuron illustrating an increasing negative offset at frequencies of 5 kHz and greater, obtained during an in vitro study in accordance with several embodiments of the present technology.
Figure 7B:
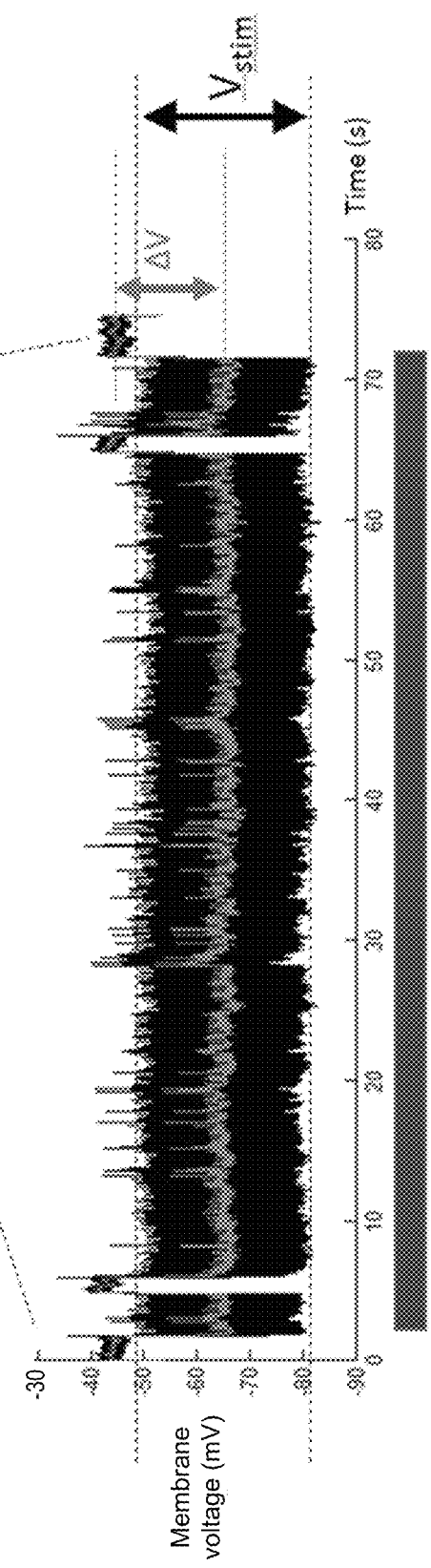
FIG. 7B is an exploded view of the diagram in FIG. 7A showing the period where a 10 kHz electric field is applied, illustrating the transmembrane potential and the voltage artifact of the stimulation.

FIGS. 7A and 7B depict a trace recorded from the spinal cord slice obtained using the experiments described herein. This recorded signal in FIG. 7A illustrates the transmembrane potential of quiescent neurons in the spinal cord slices in response to symmetric biphasic charge-balanced electrical energy delivery. A baseline trace of spontaneous firing events was recorded. The observed baseline trace of resting membrane voltage ranged from −45 mV to −40 mV. Using a pulse-width of 30 μs and an amplitude of 1.2 mA, frequencies of increasing magnitude (e.g., 1 kHz, 2 kHz, 5 kHz, 8 kHz and 10 kHz) were applied to the spinal cord slice and the firing events measured during each of the applied frequencies were recorded for 75 seconds. In response to 1 kHz stimulation, the hyperpolarization membrane potential was about −60 mV and the depolarization membrane potential was about −30 mV, effectively centered around approximately −45 mV. In response to 2 kHz stimulation, the hyperpolarization membrane potential was about −50 mV and the depolarization membrane potential was about −20 mV, effectively centered around approximately −35 mV. In response to 5 kHz stimulation, the hyperpolarization membrane potential was about −65 mV and the depolarization membrane potential was about −35 mV, effectively centered around approximately −50 mV. In response to 8 kHz stimulation, the hyperpolarization membrane potential was about −70 mV and the depolarization membrane potential was about −40 mV, effectively centered around approximately −55 mV. In response to 10 kHz stimulation, the hyperpolarization membrane potential was about −80 mV and the depolarization membrane potential was about −50 mV, effectively centered around approximately −65 mV. Following each change in frequency, the spinal cord slice was re-equilibrated to baseline and the resting membrane potential was recorded for 10 seconds.

FIG. 7B is an exploded view of the 10 kHz trace discussed above. The measured response to the symmetric biphasic charge-balanced electrical energy delivery is the sum of the applied energy delivery voltage (e.g., the voltage artifact of the delivered energy) and the transmembrane potential. In some embodiments, the voltage artifact ($V_{stim}$) corresponds the peak-to-peak amplitude of the signal. The transmembrane potential corresponds to the average, midpoint or offset voltage change (AV) of the recorded signal, i.e., the voltages around which the hyperpolarization and depolarization voltages were centered, as listed above.

While not intending to be limited to a particular mechanism of action, at frequencies at or above 5 kHz, a hyperpolarization effect can be detected in quiescent neurons within tens of milliseconds of applying the frequency, as indicated by the downward shift of the membrane voltage traces compared to stimulation frequencies of 1 kHz and 2 kHz. Despite nearly instantaneous changes in response to the applied frequency, the effect of the frequency (e.g., pain relief) may be experienced at some time after the change in transmembrane potential. In other words, the applied high frequency energy may have an instantaneous effect on pain-mediating dorsal horn neurons, but the resulting pain relief is appreciated after initiation of a cascade of secondary physiologic effects following the hyperpolarization. The AV values (from resting potentials) were estimated based on the measurements shown in FIG. 7A to predict the effect of frequency and amplitude on the responses of quiescent neurons to stimulation with kHz frequencies.

Figure 8:
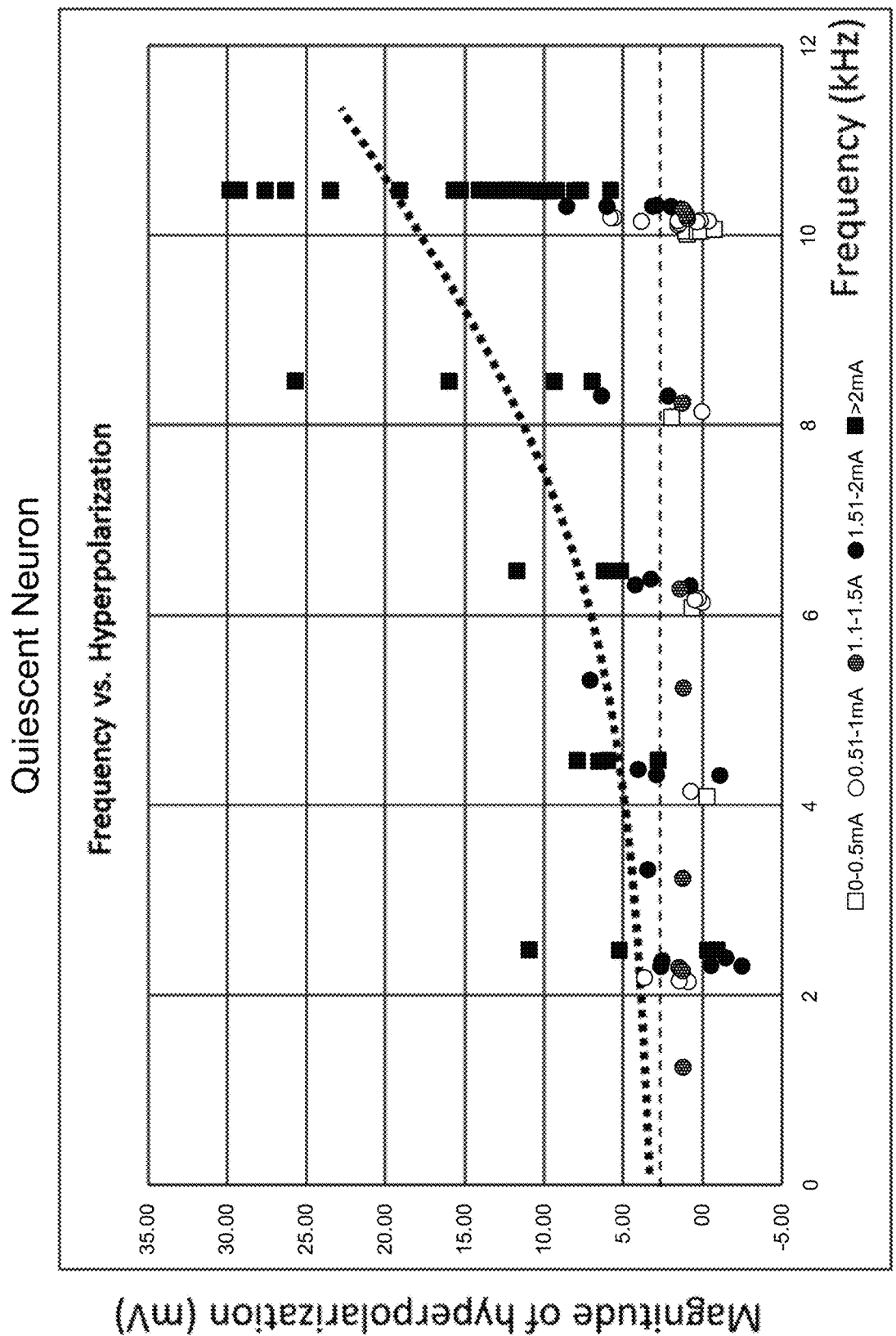
FIG. 8 is a chart illustrating the relationship between frequency and hyperpolarization for quiescent neurons and in particular, depicting the magnitude of hyperpolarization increases with increasing amplitude and increasing frequency obtained during an in vitro study in accordance with several embodiments of the present technology.

FIG. 8 is a chart illustrating the effect of frequency and amplitude on quiescent cells, based on the experiments described above with reference to FIGS. 3A and 3B. Quiescent cells were stimulated with frequencies ranging between 1 kHz and 10 kHz, inclusive, at amplitudes ranging from 0-0.5 mA, 0.51-1 mA, 1.1-1.5 mA, 1.5-2 mA and greater than 2 mA. For purposes of illustration, the frequency values for some data points were shifted slightly higher to allow other values at the same frequency to be visible. The frequencies for each of the amplitude ranges were plotted as a function of the magnitude of hyperpolarization. A hyperpolarization trend was observed for amplitudes greater than 1.5 mA, with nominal hyperpolarization detected at amplitudes of 1.5-2 mA and strong hyperpolarization detected at amplitudes greater than 2 mA. The magnitude of hyperpolarization at amplitudes from 1.5-2 mA slightly correlated with increasing frequency. The magnitude of hyperpolarization at amplitudes greater than 2 mA strongly correlated with increasing frequency.

In some embodiments, the trends shown in FIG. 8 (for quiescent neurons) are expected to be predictive of the magnitude of depolarization sufficient to inhibit spontaneous firing events in spontaneously active neurons. While not intending to be limited or bound by any particular theory, the inhibition of spontaneous firing events is expected to be a direct effect of the high frequency (e.g., kHz) neuronal stimulation, and is expected to produce therapeutic results, including but not limited to pain relief. A further discussion of the effects of HF stimulation on spontaneously firing neurons is provided later with reference to FIGS. 4-6B.

ii. Representative Computational Model Data

Figure 11A:
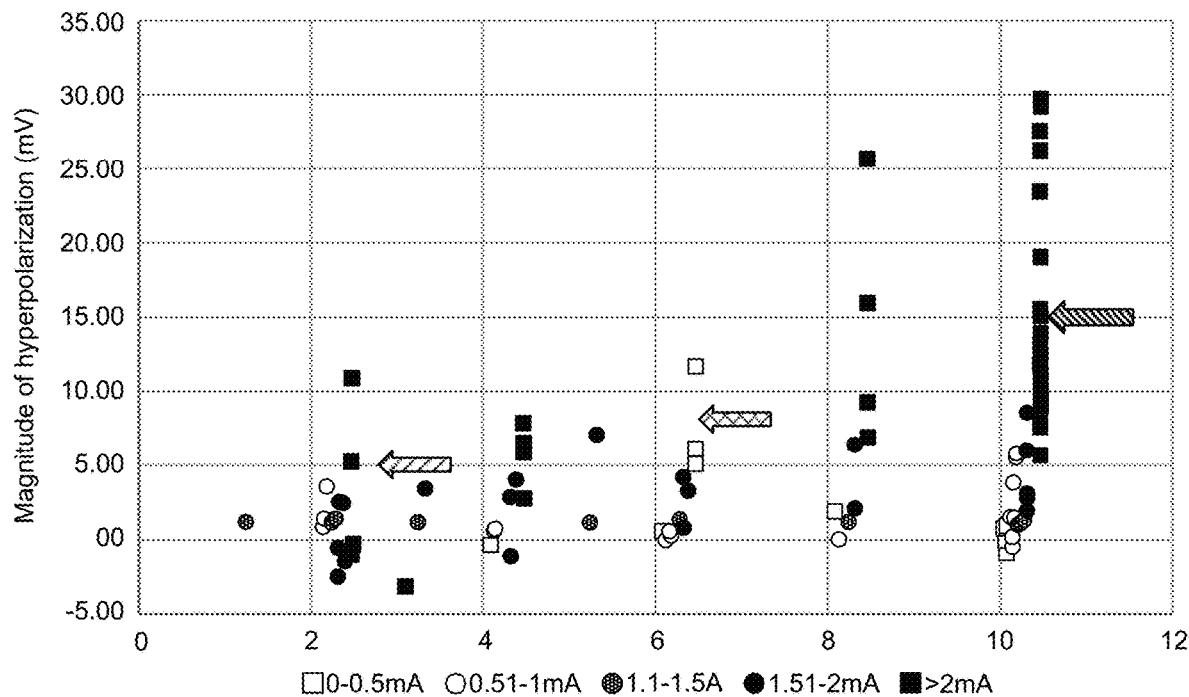
FIG. 11A is the chart of FIG. 8 including three arrows corresponding to the arrows on the x-axis and y-axis of FIG. 11B in accordance with several embodiments of the present technology.
Figure 11B:
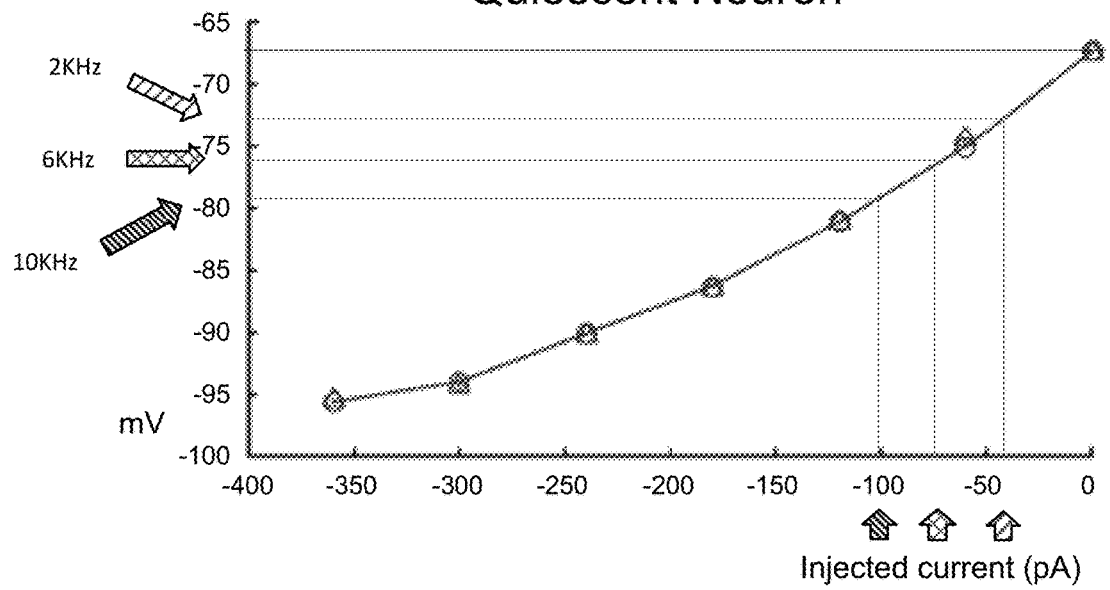
FIG. 11B is a graph of current injected into a neuron versus the membrane potential. The magnitude of hyperpolarization from FIG. 11A can be subtracted from the resting membrane potential of the y-axis (arrows) and the standard curve used to determine a computationally injected current of the x-axis (arrows) in accordance with several embodiments of the present technology.

FIGS. 11A and 11B illustrate a method for determining a kHz frequency equivalent current using (a) the computational model described above and (b) the graph depicted in FIG. 11B, which illustrates membrane potential (y-axis) as a function of injected current (x-axis) from a real quiescent neuron. First, certain kHz frequency values of interest from the Frequency vs. Hyperpolarization plot of quiescent neurons depicted in FIG. 8 were selected, for example, 2 kHz, 6 kHz and 10 kHz (indicated by the arrows in FIG. 11A). According to FIG. 11A, a frequency of 2 kHz corresponds to an average magnitude of hyperpolarization of 5 mV, a frequency of 6 kHz corresponds to an average magnitude of hyperpolarization of about 7 mV, and a frequency of 10 kHz corresponds to an average magnitude of hyperpolarization of 15 mV. Third, the magnitude of hyperpolarization for each frequency value of interest was subtracted from −68 mV, i.e., the normal resting potential of a quiescent neuron, to determine three y-axis values of −73 mV, −76 mV and −79 mV, respectively. Forth, the I-V curve of FIG. 11B was used to determine equivalent current injected into a resting quiescent neuron on the x-axis, measuring the hyperpolarized membrane potential in mV. FIG. 11B graphically illustrates using the measured resting voltage at different injected currents on a real neuron and results in estimated injected currents of −48 pA, −75 pA and −100 pA, based on the voltage change during 2 kHz, 6 kHz, and 10 kHz stimulation. Based on the foregoing technique, the computational model (calibrated with experimental data) can be used to predict the effect of applying therapy signals having a variety of signal delivery parameters to a variety of cell types.

The frequencies, pulse widths and amplitudes depicted in FIGS. 11A and 11B are not intended to limit the scope of the present technology. The units and orders of magnitude of the foregoing disclosure, for example, as illustrated in FIGS. 8, 11A, and 11B, are representative and not intended to limit the scope of the computational model as applied to the present technology or future technologies. The foregoing disclosure is rather a model application of the computational model and is intended to apply to a broad scope of frequencies, amplitudes, and other parameters.

C. Spontaneously Active Neurons i. Representative Experimental Data

Figure 4A:
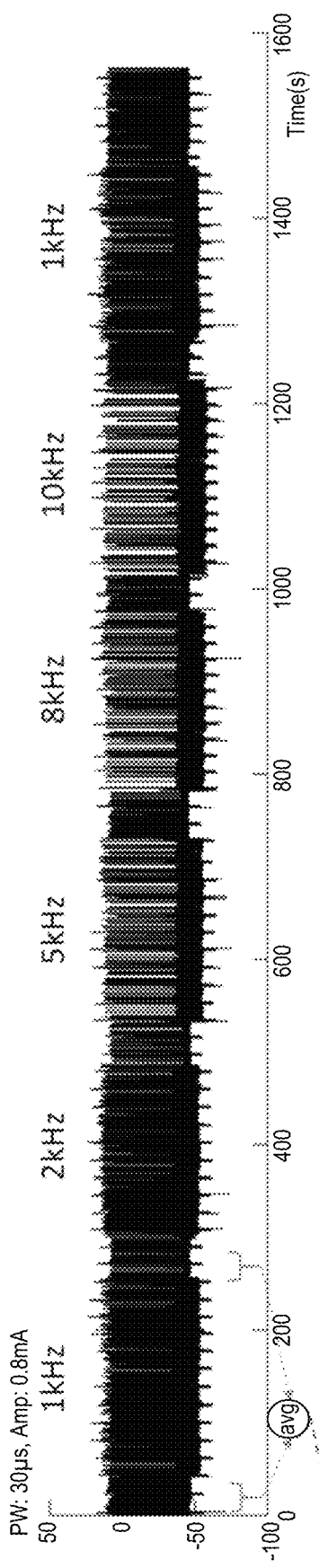
FIG. 4A is a diagram of an electrophysiological recording of a spontaneously active neuron identifying inhibition of spontaneous firing events with high frequency electric fields obtained during an in vitro study in accordance with several embodiments of the present technology.

FIG. 4A illustrates a trace recorded from the spinal cord slice obtained as a result of the experiments described herein. First, a baseline trace of spontaneous firing events was recorded (see the left side of the trace) at −50 mV. Then, using a pulse-width of 30 µs and an amplitude of 0.8 mA, a signal having a frequency of increasing magnitude (e.g., 1 kHz, 2 kHz, 5 kHz, 8 kHz and 10 kHz) was applied to the spinal cord slice, and the firing events at each of the frequencies were recorded for 200 seconds. Following each change in frequency, the spinal cord slice was re-equilibrated to baseline and the spontaneous firing rate recorded for 50 seconds. At frequencies of 5 kHz and greater, spontaneous firing events in spontaneously active neurons were inhibited, as indicated by the reduction in the number of "spikes" shown in the trace.

Figure 4B:
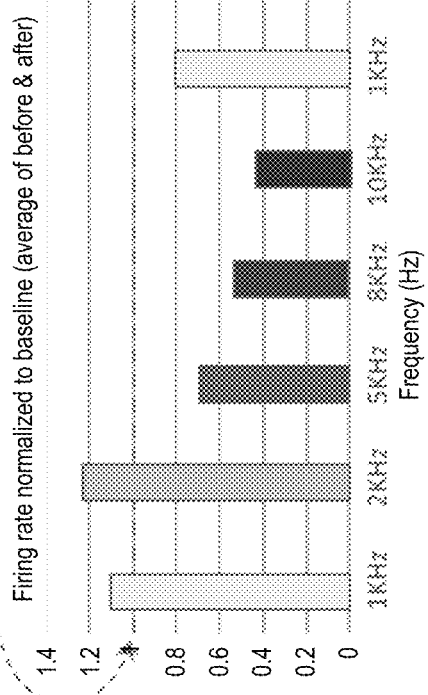
FIG. 4B is a chart illustrating the firing rate of the spontaneously active neuron normalized to a baseline of the diagram in FIG. 4A.

The graph shown in FIG. 4B is based on the trace above, and illustrates that applying a kHz field (e.g., a field created by a signal having a frequency of at least 1,000 Hz) to a spontaneously active neuron inhibits spontaneous firing events. In addition, the level of inhibition is roughly a linear function of frequency. As shown in FIG. 4A, the spontaneous firing events are inhibited quickly—seconds, milliseconds, or microseconds after a kHz frequency is applied to a spontaneously firing neuron.

Figure 5:
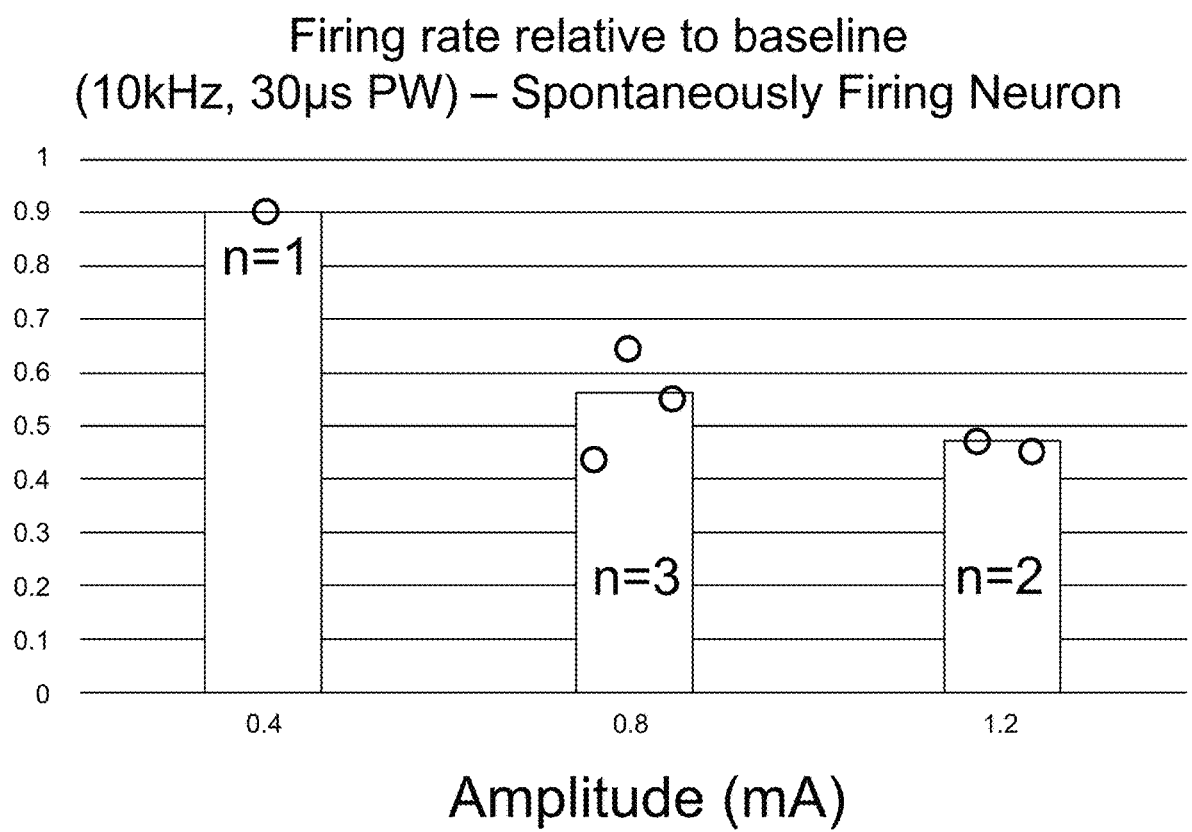
FIG. 5 is a chart illustrating the firing rate of the spontaneously active neuron of FIG. 6, normalized to a baseline, at three different amplitudes in accordance with several embodiments of the present technology.
Figure 6A:
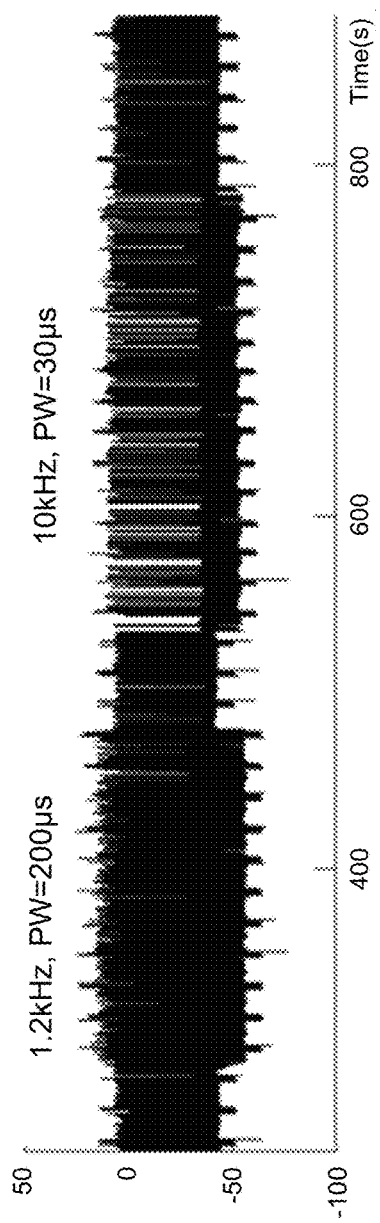
FIG. 6A is a diagram of an electrophysiological recording of a spontaneously active neuron identifying (a) inhibition of spontaneous firing events produced by high frequency electric pulses with a small pulse width and (b) no inhibition when exposed to low frequency electric pulses having a large pulse width, obtained during an in vitro study in accordance with several embodiments of the present technology.
Figure 6B:
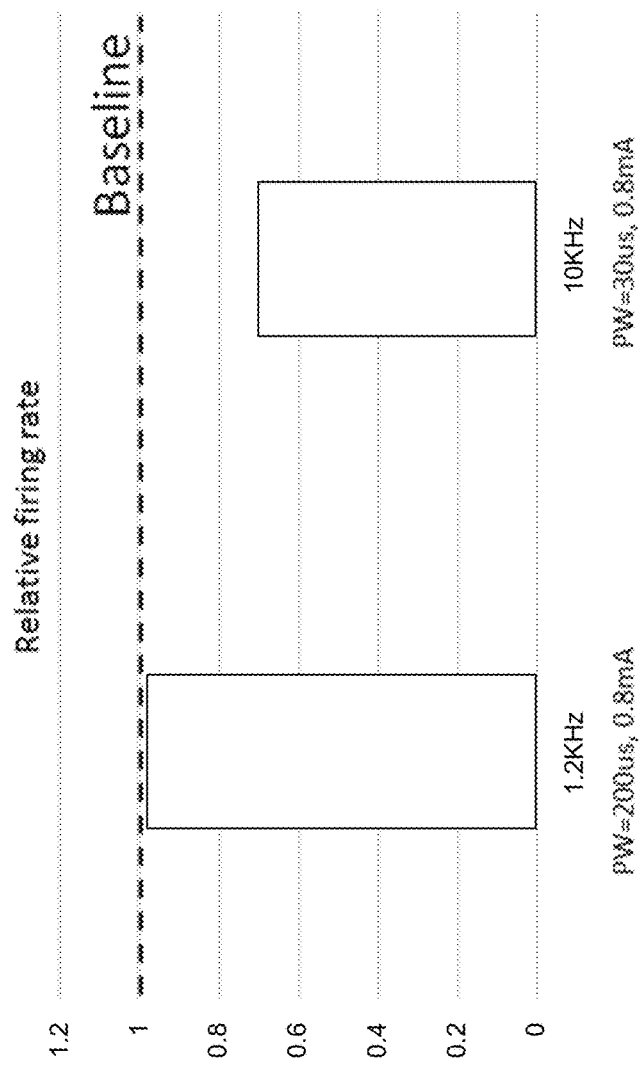
FIG. 6B is a chart illustrating the firing rate of the spontaneously active neuron normalized to a baseline of the diagram in FIG. 6A.

FIGS. 5 and 6A, 6B depict the response of spontaneously firing neurons to different amplitudes, pulse widths, frequencies and combinations thereof. FIG. 5 depicts the effect of amplitude on spontaneous firing rate in spontaneously active neurons. In response to an applied electrical energy signal having a frequency of 10 kHz and a 30 µs pulse width, the spontaneous firing rate decreases as the stimulation amplitude increases from 0.4 mA, to 0.8 mA and to 1.2 mA.

As FIG. 6A illustrates, a baseline trace of spontaneous firing events in a spinal cord slice using the experimental tissue-based model was recorded first. Second, a signal having a frequency of 1.2 kHz and a pulse width of 200 µs was applied to the spontaneously active neurons. As shown in both the trace of FIG. 6A and the bar graph of FIG. 6B, this signal failed to significantly inhibit the rate of spontaneous firing events. Third, the spontaneously active neurons were equilibrated to baseline and the spontaneous firing rate recorded for 50 seconds. Last, a signal having a frequency of 10 kHz and a pulse width of 30 µs was applied to the spontaneously active neurons. This signal clearly inhibited the rate of spontaneous firing events.

FIGS. 6A and 6B indicate that shorter pulse widths and higher frequencies are effective for inhibiting spontaneous firing rates. While not intending to be limited to a particular mechanism of action, FIGS. 6A and 6B illustrate that high frequency stimulation (e.g., 10 kHz) with smaller pulse widths (e.g., 30 µs) at 0.8 mA inhibits spontaneous firing events in spontaneously active neurons. FIGS. 6A and 6B also illustrate that low frequency stimulation (e.g., 1.2 kHz) with larger pulse widths (e.g., 200 µs) at 0.8 mA fails to inhibit spontaneous firing events in spontaneously active neurons. Although the total charge applied to the tissue at high frequency is about 20% larger than at low frequency, this nominal difference is not expected to produce the observed difference in tissue response. Instead, it is expected that the higher frequency and/or narrower pulse width are responsible. In some embodiments, high frequency stimulation can directly affect the cellular membrane.

The application of an external electrical field to a membrane has not previously been observed to have a 'rectifying' characteristic, e.g., a membrane potential response that changes in single direction, despite an applied bipolar applied electric field.

ii. Representative Embodiments of the Computational Models

Figure 12A:
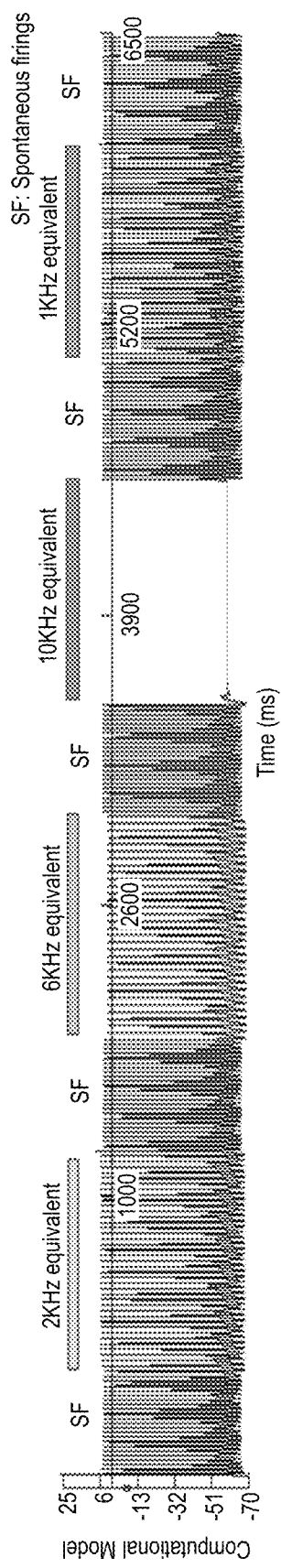
FIG. 12A is a diagram of a computational electrophysiological trace, showing similar effects as those from the in vitro study depicted in FIG. 12B, in accordance with several embodiments of the present technology.
Figure 12B:
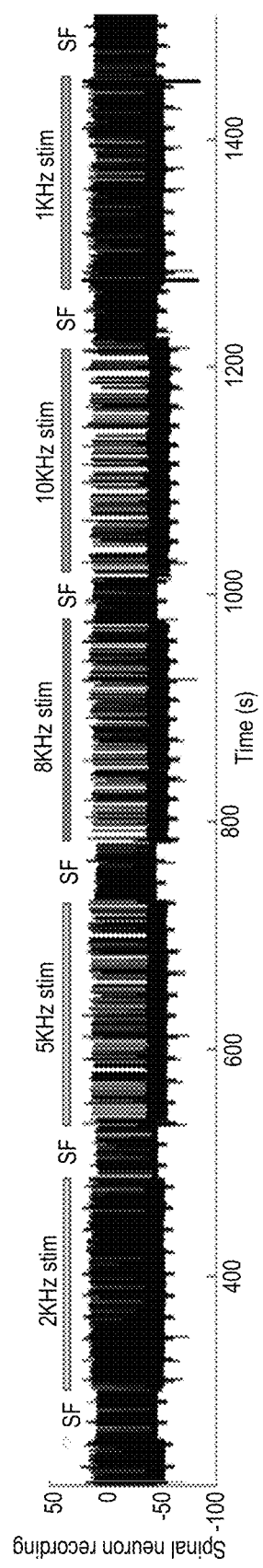
FIG. 12B is a diagram of an experimental electrophysiological recording illustrating the inhibitory effect of increasing frequency on spontaneous neuron firing, obtained during an in vitro study.

FIG. 12A depicts a computational trace of a spontaneously firing neuron generated using the computational model described above. FIG. 12B illustrates an experimentally-obtained recording of a spinal neuron obtained using the experiments described herein. Initial results from the computational model illustrate the magnitude of hyperpolarization and depolarization of a neuron while it spontaneously fires, and the response of that neuron to an injection current equivalent to the measured magnitude of hyperpolarization described above with reference to FIG. 7A and FIG. 7B. As depicted in FIG. 12A, the rate of spontaneous firing decreases as the frequency equivalent increases, for example, from 2 kHz to 6 kHz and back to 1 kHz, with a rest period in between frequency changes to allow the neuron to return to a spontaneously firing baseline. The computational model provides reliable predictions which simulate the tissue-based spinal neuron recording for 1 kHz, 2 kHz and 8 kHz. Such predictions illustrate that the firing rate of spontaneously firing neurons can be reproduced to show spontaneous firing inhibition by stimulation equivalents in the kHz range of current injection. Additional analysis of the computational model and associated results are ongoing for frequencies equivalent to 10 kHz and greater, but the initial illustrated computational results clearly predict a continued trend of further spontaneous firing inhibition at 10 kHz.

3.0 Representative Clinical Applications

This section describes observations and representative clinical applications that are based, at least in part, on the data described above. For ease of understanding, the descriptions are grouped under certain headings, but it will be understood that aspects of the technology described under one heading can supplement, complement and/or overlap with aspects described under another heading.

A. Cell Pre-Conditioning

One observation based on the results discussed above with reference to FIGS. 1-12B is that high frequency stimulation can change the local membrane potential of a neuron. For example, FIG. 8 illustrates the magnitude of membrane hyperpolarization in a quiescent neuron as a function of frequency and amplitude. When the local membrane potential changes, the effect is to modulate ion channel gating for a variety of types of ion channels. In addition, the hyperpolarization can have an effect (e.g., a concurrent effect) on several types of channels. The effects on the ion channels can in turn affect the ability of the neurons to generate action potentials.

Another application of the ability of high frequency stimulation to change membrane potential is to pre-condition the target cell in advance of another, subsequent intervention. The subsequent intervention can be electrical, chemical, and/or mechanical, but in any of the foregoing embodiments, pre-conditioning the cell (e.g., by increasing the membrane permeability of the cell to selected ions and/or other agents) can be used to clinical advantage. In one specific example, increasing the membrane permeability can increase the amount of an intrathecally-delivered drug that passes through the cell membrane. As a result, the administered amount of the drug required to achieve the target therapeutic effect can be reduced, compared to delivering the drug to a cell that has not been pre-conditioned. A follow-on result is that, in cases for which the drug has an undesirable side effect, that side effect can be reduced. This use of high frequency signals to pre-condition the cell can have particular applicability to intrathecal drug delivery, (which is typically highly localized), and/or to other delivery modalities.

In further particular embodiments, the effect of high frequency stimulation can be localized at a more granular level than the cellular level. For example, the delivered energy can be particularly applied to the cell body or soma (as opposed to the axon or dendrite) to achieve the intended affect. Such specialized targeting can also be used to selectively or preferentially modulate a C-type neural fiber rather than other neural fibers (e.g., A-type fibers).

B. Cell Activity Suppression

The foregoing technique can be used more generally to address diseases caused by or triggered by ectopic activity (e.g., activity generated by or arising from neural populations other than those ordinarily responsible for a particular function). Representative medical indications include cardiac arrhythmia, epilepsy, chronic pain resulting from hyperexcitabilty (e.g., in the dorsal horn or dorsal root ganglia or peripheral neuroma), spasticity, and autonomic system dysfunctions. For example, a neurogenic overactive bladder disorder typically includes spontaneous firing of nerves that supply the bladder. Accordingly, high frequency stimulation can be used to improve detrusor-sphincter dyssynergia (DSD). Another representative target indication includes movement disorders, including, but not limited to spasticity and/or dystonia resulting from spinal cord injury or other conditions. The typical conventional technique for dealing with this condition is to block sphincter activity (e.g., because the sphincter activity is not coordinated) and then remove the conduction block so that the initial activity is coordinated. It is expected that high frequency stimulation can have a similar affect by suppressing or inhibiting spontaneous firing, as discussed above with reference to FIGS. 4A and 4B. With the spontaneous neural firing suppressed, it is expected that the sphincter activity can proceed normally. In particular, normal neural signaling arising from healthy physiologic function may be processed with less or no interference from the spontaneously active 'noise' in neural circuits such as sphincter activity. Put another way, suppression of the spontaneous activity can increase the 'signal to noise ratio' in functional neural circuits by reducing the spontaneous 'noise'.

C. Synaptic Efficacy Change

A further observation from the results discussed above is that high frequency energy delivery may have a particular effect on C-type fibers ("C fibers"). C fibers are afferent fibers that convey input signals from the periphery to the central nervous system. C fibers are unmyelinated, which causes them to have slower conduction velocities, and fibers of this size category are typically responsible for conducting pain signals to the central nervous system. Because high frequency signals appear to specifically reduce the efficacy of C fibers without modulating A-type fibers ("A fibers"), this therapy may be particularly effective for addressing pain, without adversely effecting normal sensory responses.

While not intending to be bound by any particular theory, a result of the preferential effect of HF signals on C fibers may be that a patient's autonomic nerve fibers and terminals are specifically addressed. In some embodiments, disorders resulting from deficits in the autonomic nervous system may be suitable targets for high frequency stimulation, as might any dysfunction related to overactive C fibers. In these embodiments, one representative condition is obesity, and a potential target population is brown adipose tissue. An existing approach for addressing obesity is significantly lowering the temperature of brown adipose tissue (e.g., thermogenesis), but a drawback of this therapy is that the low temperatures recruit C fibers which create pain for the patient. If, in conjunction with thermotherapy, the C fibers are hyperpolarized via high frequency stimulation, the thermogenesis technique may be equally effective, but without causing pain in the patient. In particular embodiments, the therapy can be applied to a localized fat pad (e.g., in the shoulder), which is easily accessible and does not require epidural stimulation. The stimulation can instead be applied via a patch electrode so as to be entirely noninvasive.

More generally, high frequency therapy can be used to address any condition related to or caused by overactive C fibers, and can be applied at any of a variety of suitable target sites in some embodiments. Accordingly, the stimulation can be applied epidurally to modulate spinal cord networks, can be applied to the vagal nerve (the primary vagus nerve and/or branches of the vagus nerve) to modulate vagal neural signals, and/or can be applied peripherally (e.g., at a target organ) to address peripheral nerves. For example, obesity can be addressed via stimulation of a fat pad, as described above, and/or by stimulating a gastric vagus nerve. In some embodiments, the electrodes are positioned near synaptic transitions between C fiber termini and their dendritic or somatic targets. In these embodiments, the electrode positioning can target the effects of C fibers. Such targets included autonomic ganglia in the periphery, the dorsal horn, and end organs receiving autonomic input. Such targeting can allow the suppressive effect of the high frequency to occur on the C fiber axon, the presynaptic terminus, or the post-synaptic membrane.

A further potential result of the ability for high frequency simulation to target C fibers is that the range of therapies available to the patient can be increased. For example, by reducing the sensitivity of C fibers to pain inputs, the maximum of amplitude of therapeutic stimulation (or other treatment modalities that would or might otherwise cause pain) can be increased. With a wider available range of therapeutic amplitudes (and/or other therapy delivery parameters), the practitioner can increase the likelihood of identifying a successful set of treatment parameters.

Still further, the effect of high frequency stimulation on C fibers may be used as a predictor or screening tool to identify patients most likely to respond to a high frequency therapy. For example, a practitioner can measure the evoked potential from a C fiber (e.g., an accessible and/or recordable C fiber) subjected to high frequency stimulation and, based on the response indicated by the evoked potential determine whether the patient is a suitable candidate for high frequency therapy in accordance with the techniques described herein. In one embodiment, a patient can be placed under general anesthesia and a dorsal epidural electrode positioned over the lumbar spinal segments. A C fiber-intensity stimulus may be applied to the bottom of the foot or toes while monitoring the EMG from the peroneus longus muscle. A late response in the EMG would reflect C fiber activity. In the presence of effective amplitude and high frequency SCS parameters, the C fiber response in the EMG would be reduced.

D. Reduction in Neuronal Cell Spontaneous Firing

As discussed above, one observed effect of high frequency stimulation is that it can reduce spontaneous firing of overactive neurons. This result can be used to treat conditions that are caused by and/or correlated with spontaneously firing neurons, such as spasticity, essential tremor, epilepsy, Parkinson's disease, obesity (as discussed above), anxiety disorders, Alzheimer's, and/or cardiac arrhythmia, among others. In general, the technique of applying high frequency signals can be used to address ectopic neuronal activity. The stimulation can be applied to autonomic (vagal, sympathetic) nerves or the spinal cord (as discussed above), or to the target organ. Other representative dysfunctions that may be treated via SCS include bladder dysfunction and erectile dysfunction.

Still further dysfunctions may be treated by applying high frequency signals to the brain to address hemiparesis. For example, essential tremor, Parkinson's disease, and/or stroke may be addressed in this fashion. A stroke, for example, may cause hemiparesis, and a patient suffering from a right hemisphere stroke typically experiences an increased activity level in the left hemisphere to compensate for the loss of function in the right hemisphere. This somewhat redundant (though less efficient) pathway allows one hemisphere to assume some control of some functions previously controlled by the other hemisphere. However, the increased activity (i.e., compensatory neuroplasticity) in the left hemisphere may actually inhibit rehabilitative neural processes of the damaged tissue from occurring in the stroke-affected right hemisphere. Accordingly, by suppressing the compensatory activity in the left hemisphere (e.g., via high frequency stimulation), the right hemisphere can be encouraged to rehabilitate. While not intending to be limited to any particular theory, the present technology may treat the hem iparesis features rather than the spastic features of stroke. The stimulation can be applied cortically via a cortical electrode, or to the deep brain via a deep brain probe.

Tinnitus is another example of a dysfunction that may be addressed via brain stimulation and/or vagus nerve stimulation. Tinnitus (which is often perceived as a ringing in the ears) may result from a loss of sensory input to the auditory cortex, resulting in aberrant neural activity that is perceived by patients. Accordingly, applying high frequency stimulation may reduce the high activity level, based on the effect of high frequency stimulation on spontaneous neural firings. Phantom limb pain also results from neuronal cell overactivity (e.g., neurons operating in an open loop, without appropriate sensory inputs), and can accordingly also be addressed via high frequency stimulation. Phantom limb pain can also be addressed with epidural stimulation. For example, ectopic signals emanating from dorsal root ganglion and/or the neuroma can be effectively suppressed with a 10 kHz signal.

E. "Rebound" Effect

Another effect observed from the data described above is a "rebound" effect. When high frequency stimulation is applied to the target neural population, the activity level of the target cells can be suppressed or at least decreased. Once the stimulation is halted, the target cells tend to respond in a "rebound" manner, generating one or more spontaneous action potentials that appear to result solely from the sudden absence of the high frequency stimulation signal. In at least some embodiments, the action potential(s) may be perceived by the patient as pain and in other embodiments, the action potential(s) may decrease the effectiveness of SCS therapy for a patient with chronic pain. Accordingly, it may be desirable to reduce or eliminate the rebound affect. In other embodiments, for example when the inactivity of the target neuron is exhibiting an undesirable behavior, the rebound effect may be used to generate desirable action potentials that the target neuron fails to generate.

One approach for reducing or eliminating the rebound is to limit the duration of breaks in a pulse train to be at or below a threshold duration. For example, short breaks lasting less than about 5 milliseconds are not expected to result in rebound. More generally, use of short breaks in the range of about 5 milliseconds to about 15 milliseconds are expected to reduce or eliminate rebound, and breaks greater than about 30 milliseconds are not expected to reduce rebound firings.

Another approach for reducing or eliminating the rebound is to taper at least one parameter of the stimulation signal before the signal is completely halted. The signal may be completely halted for any of a number of suitable reasons, including to allow telemetry signals to be issued periodically, and/or for duty cycling, which provides an effective therapeutic result without the battery power required for delivering a continuous therapy signal. FIGS. 13A-18B illustrate representative tapered and/or otherwise modulated waveforms and the expected results therefrom.

Figures 13A, 13B:
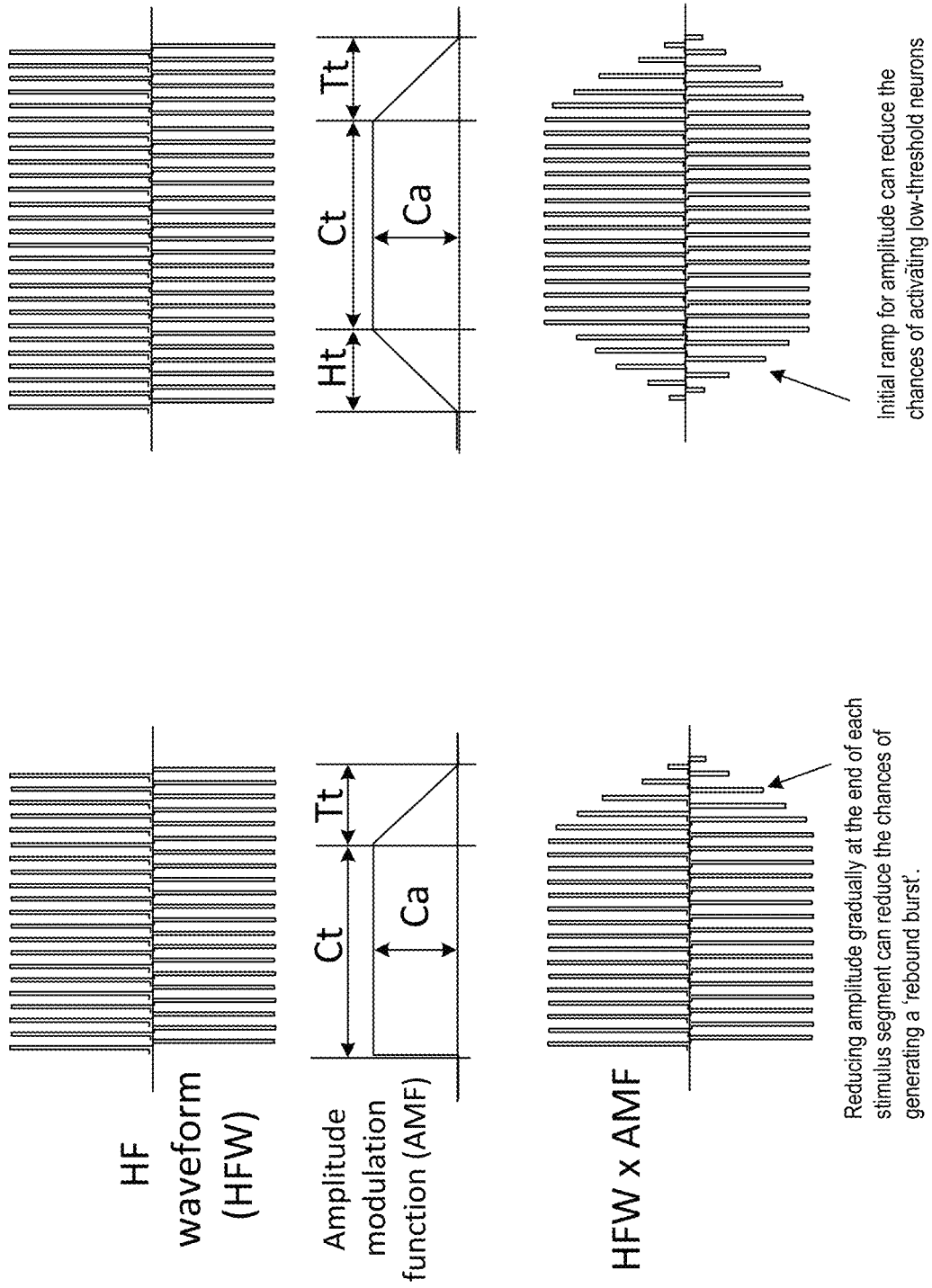
FIGS. 13A and 13B illustrate representative amplitude-modulated high frequency waveforms in accordance with embodiments of the present technology.

FIG. 13A illustrates a representative high frequency waveform (HFW) followed by a representative amplitude modulation function (AMF), and the effect of the amplitude modulation function on the high frequency waveform. As shown in FIG. 13A, the result of modulating the high frequency waveform is a series of pulses having a constant amplitude Ca over a central period Ct, and a downwardly tapering amplitude during a terminal tapering period Tt. This approach can also be applied to the initiation of the high frequency signal, as shown in FIG. 13B. In this case, the amplitude modulation function includes an initial ramp-up period Ht to produce an upwardly ramped amplitude at the outset of a particular set of pulses, in combination with the downwardly tapered amplitude at the end shown in FIG. 13A.

Figure 14:
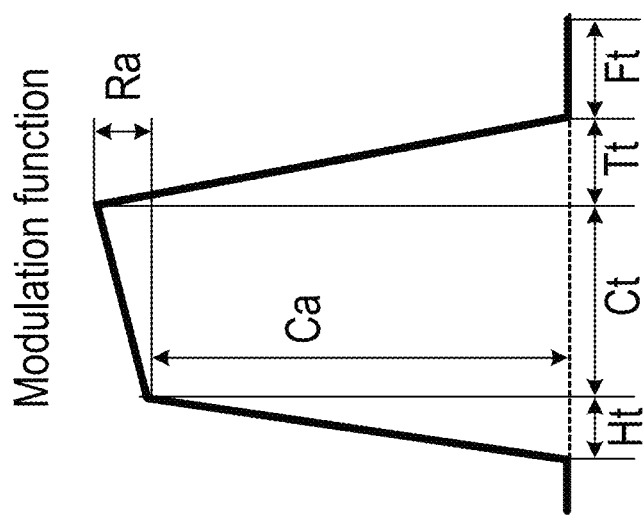
FIG. 14 illustrates an amplitude modulation function in accordance with another embodiment of the present technology.

FIG. 14 illustrates a more general modulation function that includes an initial upwardly tapering period Ht, a central period Ct, a downwardly tapering period Tt and an off period Ft. During the central period Ct, the stimulation amplitude can also change, for example, ramping upwardly as indicated by ramp amplitude Ra.

Figure 15:
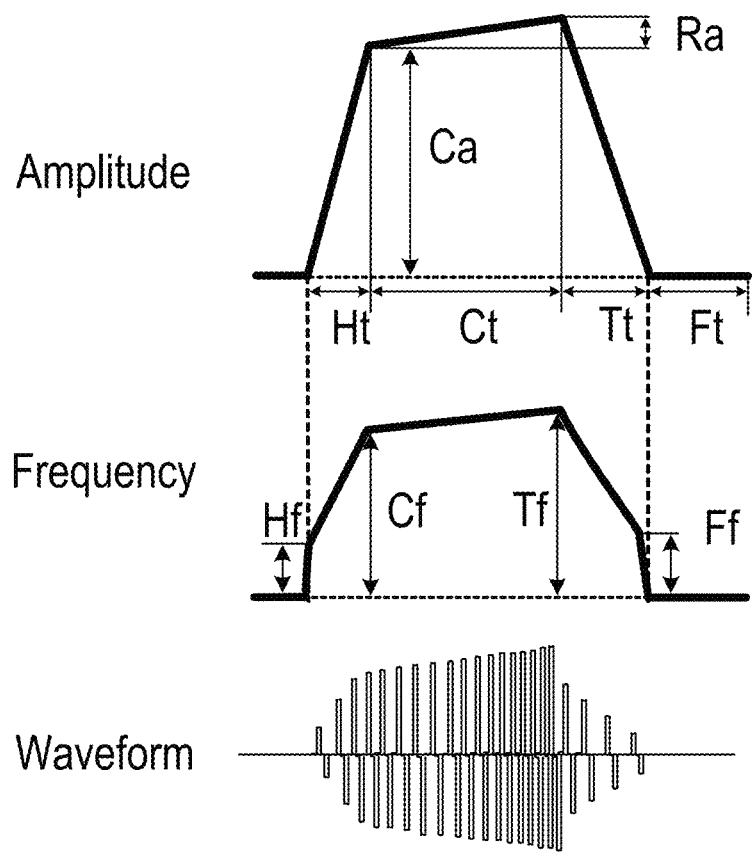
FIG. 15 illustrates the effects of amplitude and frequency modulation on a waveform in accordance with an embodiment of the present technology.

FIG. 15 illustrates two modulation functions: an amplitude modulation function and a frequency modulation function, both of which are applied to the waveform shown at the bottom of FIG. 15. As shown in FIG. 15, both the amplitude and frequency undergo a ramped increase toward the beginning of the pulse train, and a ramped decrease toward the end of the pulse train.

Figures 16A, 16B:
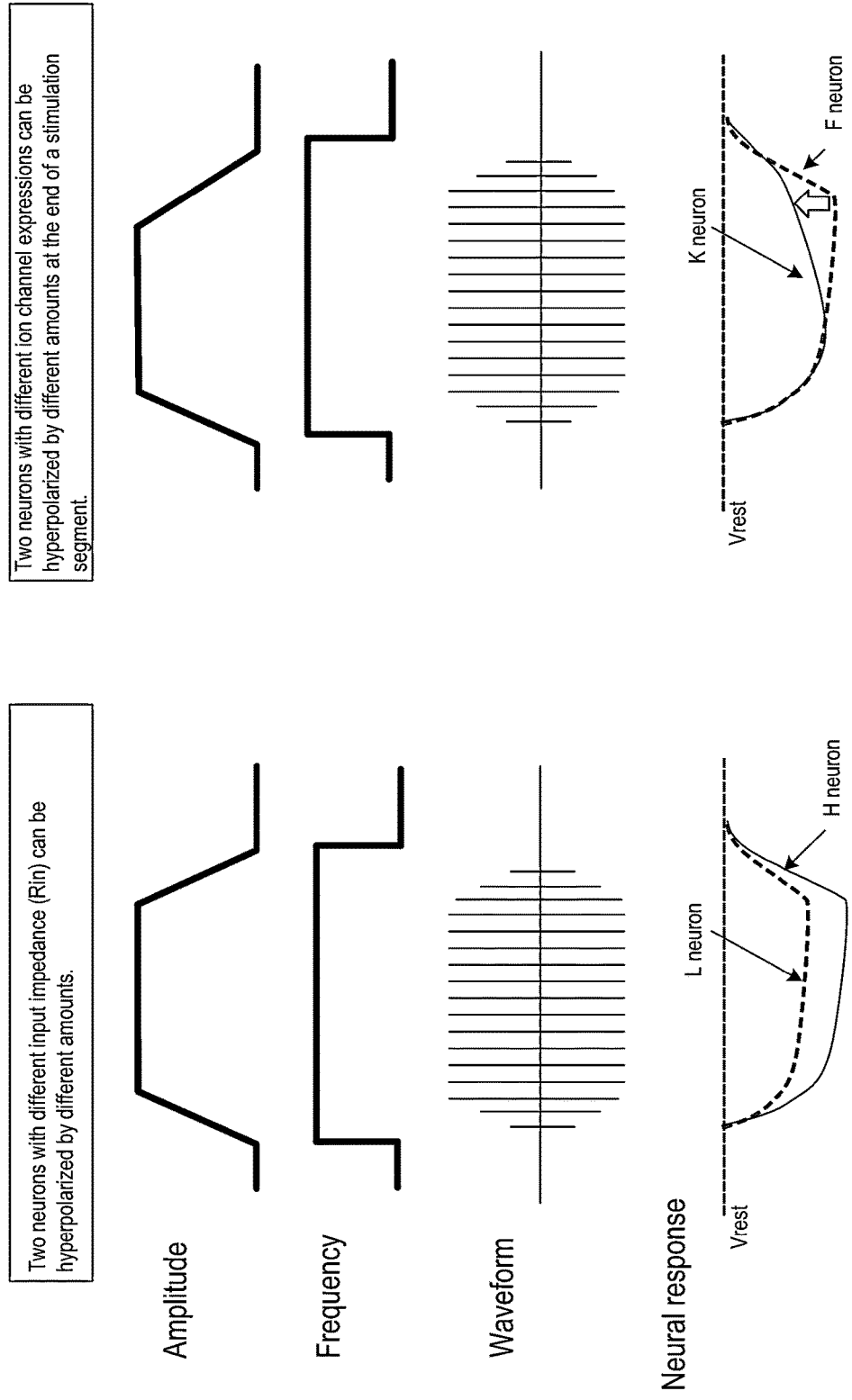
FIGS. 16A and 16B illustrate the effects of amplitude- and frequency-modulated waveforms on neurons having different input impedances and ion channel expressions, in accordance with embodiments of the present technology.

FIGS. 16A and 16B illustrate the effect of amplitude and frequency modulation on neurons having different input impedances (FIG. 16A) or different ion channel expressions (FIG. 16B). Beginning with FIG. 16A, the high frequency waveform is modified by a ramped amplitude function and a stepped frequency function. The neural response (indicating the degree of hyperpolarization from the resting potential, Vrest), can differ for neurons having different input impedances. For example, an H neuron having a higher input impedance than an L neuron may accordingly experience a greater degree of hyperpolarization.

FIG. 16B illustrates a high frequency waveform also modified by a ramped amplitude modulation function and a stepped frequency function. In this case, a representative K neuron has a higher ion channel expression than a corresponding F neuron. As a result of the greater ion channel expression, the K neuron may recover more quickly from a hyperpolarized state than the F neuron.

FIGS. 17A and 17B illustrate the combined effects of amplitude and frequency modulation on an F neuron (which is more sensitive to frequency) and an A neuron (which is more sensitive to amplitude). FIG. 17A illustrates a high frequency waveform modulated by a ramped amplitude modulation function and frequency modulation function. The A neuron, which is more sensitive to amplitude, hyperpolarizes by a greater amount initially due to the steep initial increase in amplitude, and gradually repolarizes as the amplitude gradually decreases. The F neuron, which is more frequency sensitive, hyperpolarizes gradually as a result of the gradual increase in frequency, and quickly repolarizes when the frequency undergoes a step drop. As a result of the step change in frequency, the F neuron experiences a rebound effect, illustrated by two action potentials after the high frequency wave form has ceased.

FIG. 17B illustrates the opposite effect when the amplitude undergoes a step decrease, and is ramped. In this case, the A neuron gradually becomes hyperpolarized as the amplitude gradually increases, and experiences a rebound when the amplitude is suddenly reduced, generating the two rebound action potentials shown in FIG. 17B. By contrast, the F neuron quickly reaches its hyperpolarized state due to the steep rise in frequency at the beginning of the waveform, and gradually achieves the normal resting potential as a result of the ramped decrease in frequency over the course of the stimulation.

FIGS. 18A and 18B illustrate the effect of a pulse width change on the F and A neurons described above with reference to FIGS. 17A and 17B. In general, a change in pulse width is expected to have a greater effect on the frequency-sensitive F neuron than on the amplitude-sensitive A neuron. For example, referring first to FIG. 18A, the waveform is modified by an amplitude modulation function, a frequency modulation function, and a pulse width modulation function that increases the width of the pulses approximately one third of the way through the signal delivery period. The F neuron begins depolarizing until the pulse width increases. The interruption created by the pulse width increase generates a type of rebound response, producing two action potentials, as shown in FIG. 18A. The membrane then again begins hyperpolarizing until the end of the burst. Even though the frequency decreases suddenly at the end of the burst, the F neuron has not become sufficiently hyperpolarized to generate another rebound action potential.

The A neuron depolarizes rapidly due to the ramped increase in amplitude. The increase in pulse width causes some depolarization, but not enough to trigger a rebound effect. The A neuron does not exhibit a rebound effect at the end of the burst because the amplitude is ramped downwardly.

In FIG. 18B, the pulse width increase occurs later in the burst, and accordingly delays the rebound action potentials of the F neuron. When the stimulation signal ceases, the F neuron does not trigger another rebound action potential because it has not sufficiently hyperpolarized, and because the frequency is tapered rather than stepped down.

The A neuron gradually becomes hyperpolarized as a result of the gradual amplitude ramp, partially depolarizes as a result of the increased pulse width, and then rebounds as a result of the steep drop in amplitude at the end of the burst, triggering two rebound action potentials.

It is expected that the foregoing effects (which are simulated in FIGS. 13A-18B) can be used to tailor specific waveforms to achieve specific desired effects. Accordingly, neurons that are sensitive to frequency and/or pulse widths can receive a therapy signal that is deliberately ramped in a manner that produces action potentials, or deliberately ramped in a manner that reduces the likelihood for rebound-based action potentials. Similarly, neurons that are sensitive to amplitude can be deliberately triggered via steep amplitude drops, or such rebound-based action potentials can be avoided with ramps.

F. Activating Inward Potassium Rectifier

Still another preliminary conclusion based on the foregoing data is that neuropathic pain may be tied to reduced potassium chloride cotransporter (KCC) expression, which typically works like a pump to direct ions through the membrane. Activating inward rectification may compensate for the KCC reduction. This phenomenon may explain why appropriate high frequency therapy signals can reduce pain, and may also indicate that other diseases or disease states related to KCC expression or sodium potassium chloride cotransporter (NaKCC) may be addressed with high frequency stimulation. Representative conditions include persistent hyper insulinemic hypoglycemia of infants, which relates to autosomal recessive mutations and $K_{ir}$ 6.2. Certain mutations of this gene diminish the channel's ability to regulate insulin secretion, leading to hypoglycemia. Another representative condition includes Bartter's syndrome, which may be caused by mutations in the $K_{ir}$ channels. This condition is characterized by the inability of kidneys to recycle potassium, causing low levels of potassium in the body. Anderson's syndrome is a rare condition caused by multiple mutations of $K_{ir}$ 2.1. Depending on the mutation, it can be dominant or recessive. It is characterized by periodic paralysis, cardiac arrhythmias, and/or dismorphic features. See, also, KCNJ2.

Barium poisoning may be due to the observed effect of barium as blocking $K_{ir}$ channels, and accordingly may be alleviated by a high frequency signal that activates such channels. Atherosclerosis (heart disease) may also be related to $K_{ir}$ channels. The loss of $K_{ir}$ currents and endothelial cells is one of the first known indicators of atherogensis (the initiation of heart disease). Thyrotoxic hypokalaemic period paralysis has also been linked to altered $K_{ir\,2.6}$ function, and EAST/SeSAME syndrome may be caused by mutations of KCNJ 10.

Without intending to be limited to any particular theory, the present technology may be applied to deep brain stimulation (DBS). Conventional wisdom suggests that DBS activates axons to achieve reductions in dysfunctional motor activity. Similar to SCS, DBS is thought to activate axons of passage near the electrodes, resulting in modification of the activity of distal neural circuits. Activation of the targeted axons provides a therapeutic effect by interfering with dysfunctional thalamocortical loops that create tremor and loss of motor control. However, the inadvertent activation of collateral axons may result in the side effects associated with DBS, such as paresthesia or numbness, muscle tightness of the face or arms, speech problems, balance and gait alterations, lightheadedness, and unwanted mood changes. Using high frequency modulation in accordance with embodiments of the present technology, the DBS electrodes may be positioned near the cell bodies of interest and generate an effective suppression of ectopy or passage of inappropriate signaling. In some embodiments, the effective suppression could reduce many side effects of DBS since, in accordance with such embodiments, axons that might otherwise trigger distal neural circuits unrelated to the desired therapeutic outcomes are not activated.

4.0 Representative Therapy Systems

A. Representative Systems

Figure 19:
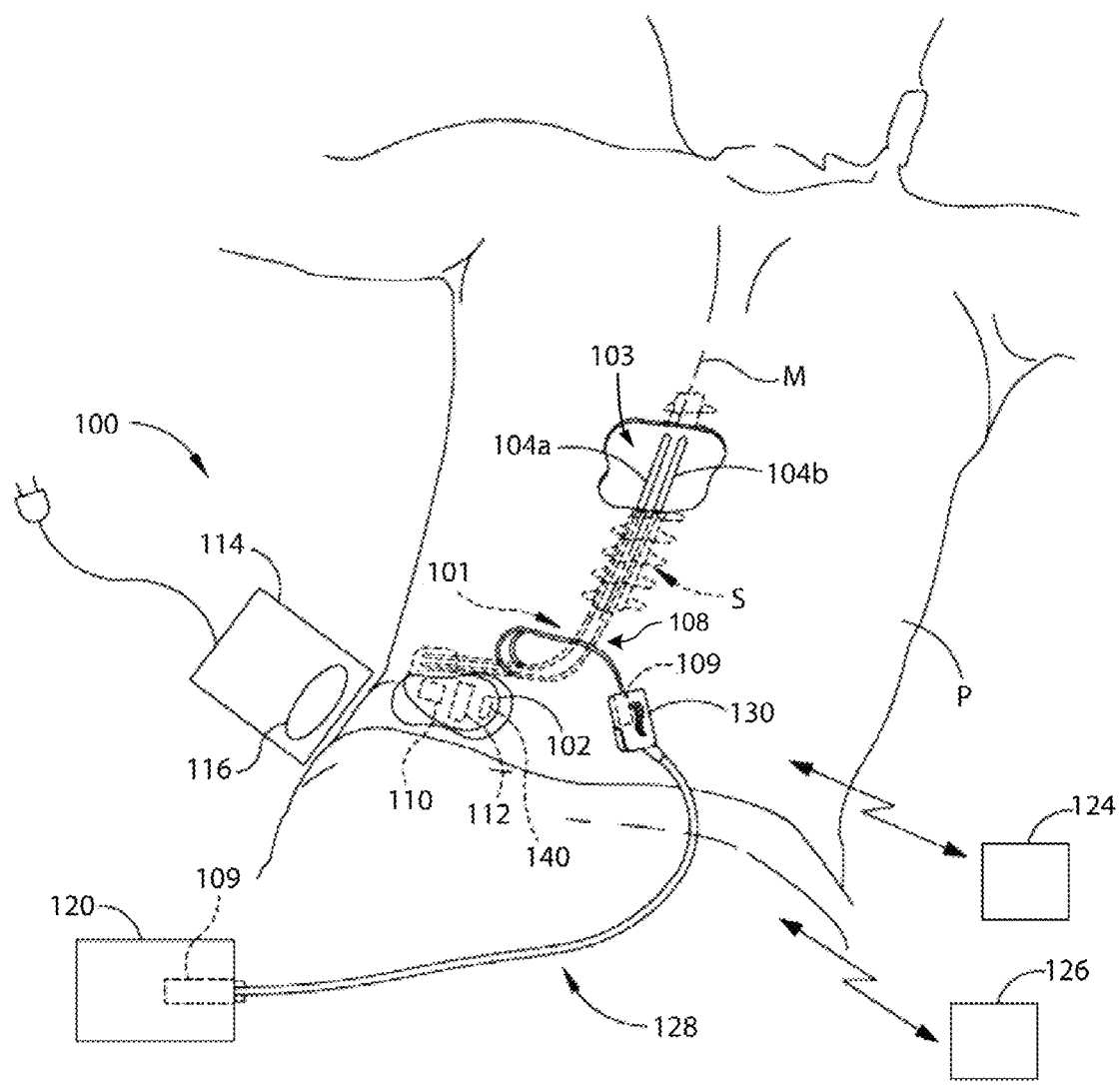
FIG. 19 is a partially schematic illustration of an implantable spinal cord stimulation system positioned to deliver therapeutic signals to the spinal cord region in accordance with several embodiments of the present technology.

FIG. 19 schematically illustrates a representative treatment system 100 for treating one or more neurologic diseases (and/or other conditions) arranged relative to the general anatomy of a patient's spinal column. The treatment system 100 can include a signal delivery system 101 having a signal generator 102 (e.g., a pulse generator) and a signal delivery device 103 comprising one or more signal delivery elements 104 (referred to individually as first and second signal delivery elements 104a, 104b, respectively). The signal generator 102 can be connected directly to the signal delivery element(s) 104, or it can be coupled to the signal delivery element(s) 104 via a signal link 108 (e.g., an extension). In some embodiments, the signal generator 102 may be implanted subcutaneously within a patient P. As shown in FIG. 19, the signal delivery element(s) 104 is configured to be positioned at or proximate to the spinal cord to apply a high frequency electrical signal to the spinal cord (e.g., to the white matter and/or glial cells of the spinal cord). It is believed that glial cells are present in large concentrations within white matter, and that high frequency modulation at or proximate the white matter can activate electrically deficient glial cells.

In a representative embodiment, the signal delivery device 103 includes the first and second signal delivery elements 104a, 104b, each of which comprises a flexible, isodiametric lead or lead body that carries features or elements for delivering an electrical signal to the treatment site after implantation. As used herein, the terms "lead" and "lead body" include any of a number of suitable substrates and/or support members that carry devices for providing therapy signals to the patient. For example, the lead body can include one or more electrodes or electrical contacts that direct electrical signals into the patient's tissue, such as to directly affect a cellular membrane. In other embodiments, the signal delivery device 103 and/or signal delivery elements 104 can include devices other than a lead body (e.g., a paddle) that also direct electrical signals and/or other types of signals to the patient. Additionally, although FIG. 19 shows an embodiment utilizing two signal delivery elements 104, in other embodiments the signal delivery system 101 and/or signal delivery device 103 can include more or fewer signal delivery elements (e.g., one signal delivery element, three signal delivery elements 104, four signal delivery elements 104, etc.), each configured to apply electrical signals at different locations and/or coordinate signal delivery to deliver a combined signal to the same (or generally the same) anatomical location.

As shown in FIG. 19, the first signal delivery element 104a can be implanted on one side of the spinal cord midline M, and the second signal delivery element 104b can be implanted on the other side of the spinal cord midline M. For example, the first and second signal delivery elements 104a, 104b shown in FIG. 19 may be positioned just off the spinal cord midline M (e.g., about 1 mm offset) in opposing lateral directions so that first and second signal delivery elements 104a, 104) are spaced apart from each other by about 2 mm. In particular embodiments, the first and second signal delivery elements 104a, 104b may be implanted at a vertebral level ranging from, for example, about T8 to about T12. In other embodiments, one or more signal delivery devices can be implanted at other vertebral levels.

The signal generator 102 can transmit signals (e.g., electrical therapy signals) to the signal delivery element 104 that up-regulate (e.g., stimulate or excite) and/or down-regulate (e.g., block or suppress) target nerves (e.g., local vagal nerves). As used herein, and unless otherwise noted, to "modulate," "stimulate," or provide "modulation" or "stimulation" to the target nerves refers generally to having either type of the foregoing effects on the target nerves. The signal generator 102 can include a machine-readable (e.g., computer-readable) medium containing instructions for generating and transmitting suitable therapy signals. The signal generator 102 and/or other elements of the treatment system 100 can include one or more processors 110, memories 112 and/or input/output devices 140. Accordingly, the process of providing electrical signals, detecting physiological parameters of the patient, adjusting the modulation signal, and/or executing other associated functions can be performed by computer-executable instructions contained by computer-readable media located at the signal generator 102 and/or other system components. The signal generator 102 can include multiple portions, elements, and/or subsystems (e.g., for directing signals in accordance with multiple signal delivery parameters) housed in a single housing, as shown in FIG. 19, or in multiple housings.

The signal delivery system 101 can include one or more sensing elements for detecting one or more physiological parameters of the patient before, during, and/or after the application of electrical therapy signals. In some embodiments, one or more of the sensing elements can be carried by the signal generator 102, the signal delivery element 104, and/or other implanted components of the system 101. In other embodiments, the sensing element(s) can be an extracorporeal or implantable device separate from the signal generator 102 and/or signal delivery element 104.

Representative sensing elements 140 include one or more of: a subcutaneous sensor, a temperature sensor, an impedance sensor, a chemical sensor, a biosensor, an electrochemical sensor, a hemodynamic sensor, an optical sensor and/or other suitable sensing devices. Physiological parameters detected by the sensing element(s) 140 include neurotransmitter concentration, local impedance, current, and/or voltage levels, and/or any correlates and/or derivatives of the foregoing parameters (e.g., raw data values, including voltages and/or other directly measured values).

The signal generator 102 can also receive and respond to one or more input signals received from one or more sources. The input signals can direct or influence the manner in which the therapy and/or process instructions are selected, executed, updated, and/or otherwise performed. The input signals can be received from one or more sensors (e.g., the input device 140 shown schematically in FIG. 19 for purposes of illustration) that are carried by the signal generator 102 and/or distributed outside the signal generator 102 (e.g., at other patient locations) while still communicating with the signal generator 102. The sensors and/or other input devices 140 can provide inputs that depend on or reflect patient state (e.g., patient position, patient posture, and/or patient activity level), and/or inputs that are patient-independent (e.g., time). Still further details are included in U.S. Pat. No. 8,355,797, which is incorporated herein by reference in its entirety.

In some embodiments, the signal generator 102 can obtain power to generate the therapy signals from an external power source 114. The external power source 114 can transmit power to the implanted signal generator 102 using electromagnetic induction (e.g., RF signals). For example, the external power source 114 can include an external coil 116 that communicates with a corresponding internal coil (not shown) within the implantable signal generator 102. The external power source 114 can be portable for ease of use.

In another embodiment, the signal generator 102 can obtain the power to generate therapy signals from an internal power source, in addition to or in lieu of the external power source 114. For example, the implanted signal generator 102 can include a non-rechargeable battery or a rechargeable battery to provide such power. When the internal power source includes a rechargeable battery, the external power source 114 can be used to recharge the battery. The external power source 114 can in turn be recharged from a suitable power source (e.g., conventional wall power).

During at least some procedures, an external programmer 120 (e.g., a trial modulator) can be coupled to the signal delivery element 104 during an initial procedure, prior to implanting the signal generator 102. For example, a practitioner (e.g., a physician and/or a company representative) can use the external programmer 120 to vary the modulation parameters provided to the signal delivery elements 104 in real time, and select optimal or particularly efficacious parameters. These parameters can include the location from which the electrical signals are emitted, as well as the characteristics of the electrical signals provided to the signal delivery elements 104. In some embodiments, input is collected via the external programmer and can be used by the clinician to help determine what parameters to vary. In a typical process, the practitioner uses a cable assembly 128 to temporarily connect the external programmer 120 to the signal delivery element 104. The practitioner can test the efficacy of the signal delivery elements 104 in an initial position. The practitioner can then disconnect the cable assembly 128 (e.g., at a connector 130), reposition the signal delivery elements 104, and reapply the electrical signal. This process can be performed iteratively until the practitioner obtains the desired signal parameters and/or position for the signal delivery element 104. Optionally, the practitioner can move the partially implanted signal delivery element 104 without disconnecting the cable assembly 128. Furthermore, in some embodiments, the iterative process of repositioning the signal delivery devices 110 and/or varying the therapy parameters may not be performed.

After the signal delivery elements 104 are implanted, the patient P can receive therapy via signals generated by the external programmer 120, generally for a limited period of time. During this time, the patient wears the cable assembly 128 and the external programmer outside the body. Assuming the trial therapy is effective or shows the promise of being effective, the practitioner then replaces the external programmer 120 with the implanted signal generator 102, and programs the signal generator 102 with therapy programs selected based on the experience gained during the trial period. Optionally, the practitioner can also replace the signal delivery elements 104. The signal delivery parameters provided by the signal generator 102 can still be updated after the signal generator 102 is implanted, via a wireless physician's programmer 124 (e.g., a physician's remote) and/or a wireless patient programmer 126 (e.g., a patient remote). Generally, the patient P has control over fewer parameters than does the practitioner. For example, the capability of the patient programmer 126 may be limited to starting and/or stopping the signal generator 102, and/or adjusting the signal amplitude. The patient programmer 126 may be configured to accept pain relief input as well as other variables, such as medication use.

The signal generator 102, the lead extension, the external programmer 120 and/or the connector 130 can each include a receiving element 109. Accordingly, the receiving elements 109 can be patient implantable elements, or the receiving elements 109 can be integral with an external patient treatment element, device or component (e.g., the external programmer 120 and/or the connector 122). The receiving elements 109 can be configured to facilitate a simple coupling and decoupling procedure between the signal delivery elements 104, the lead extension, the pulse generator 101, the trial modulator 105 and/or the connector 122. The receiving elements 109 can be at least generally similar in structure and function to those described in U.S. Patent Application Publication No. 2011/0071593, incorporated by reference herein in its entirety.

5.0 Representative Clinical Embodiments

A. Spinal Location and Vagus Nerve

Figure 20:
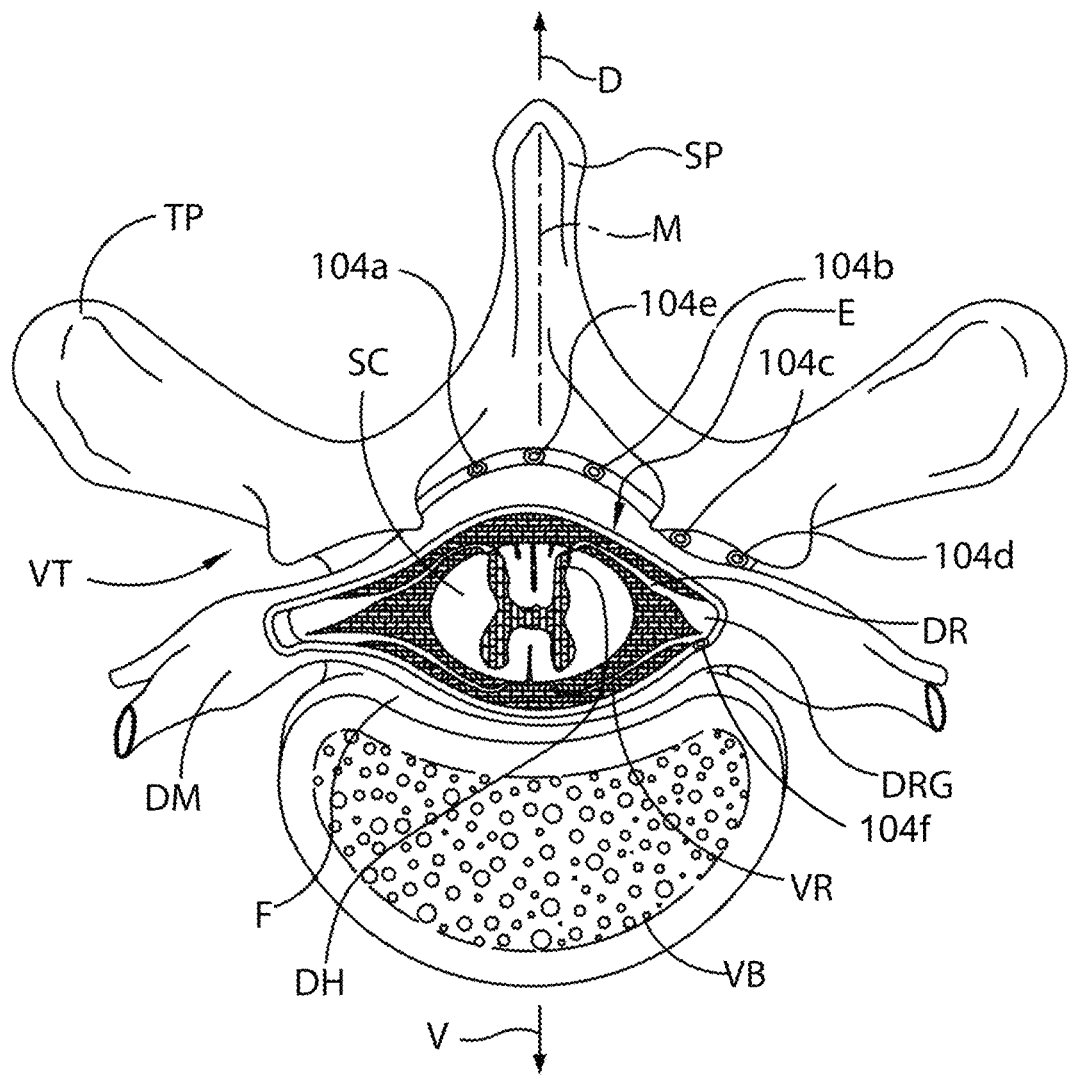
FIGS. 20-21 are partially schematic, cross-sectional illustrations of a patient's spine, illustrating representative locations for implanted signal delivery devices in accordance with several embodiments of the present technology.
Figure 21:
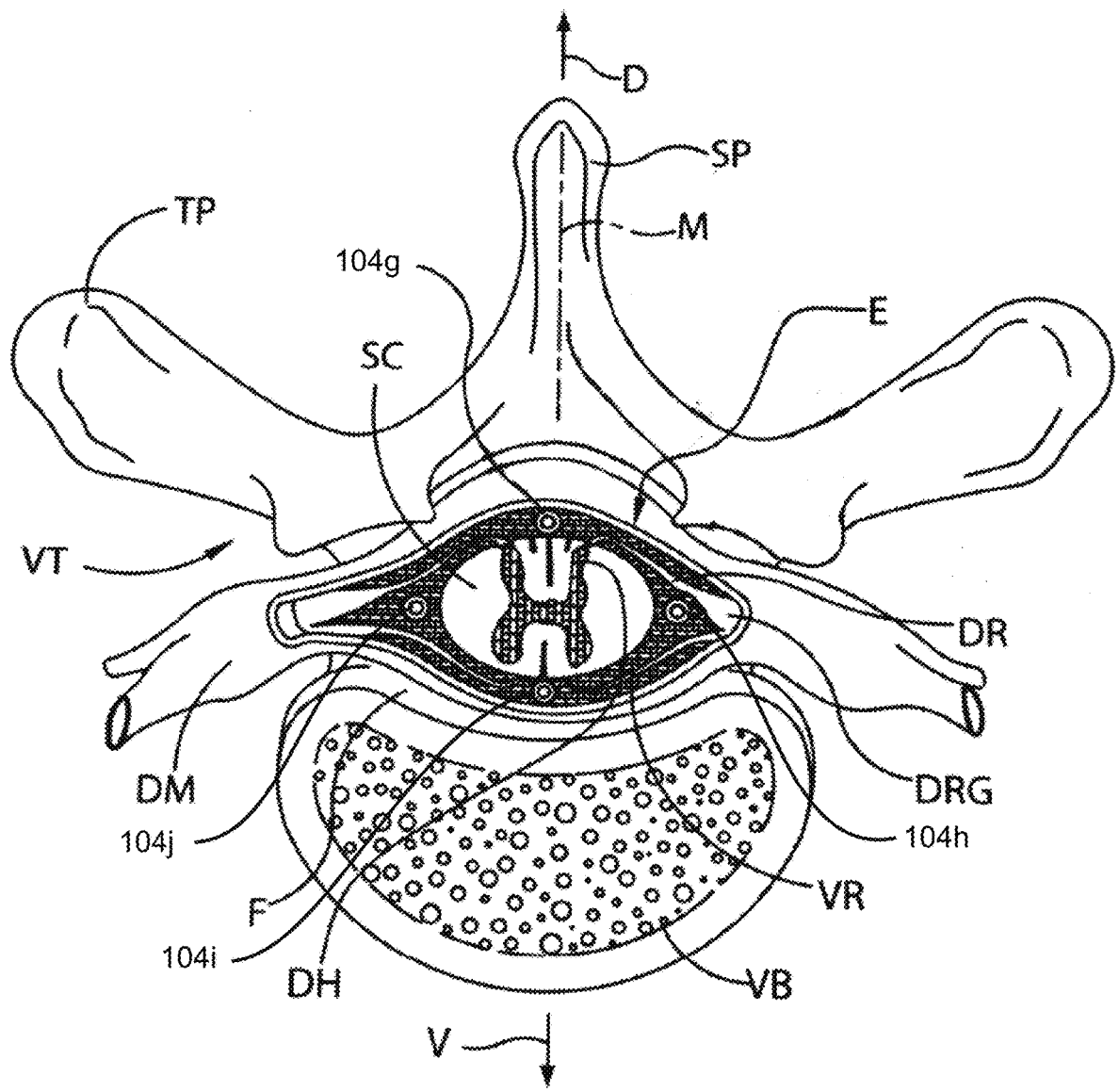

FIG. 20 is a cross-sectional illustration of a spinal cord SC and an adjacent vertebra VT (based generally on information from Crossman and Neary, "Neuroanatomy," 1995 (published by Churchill Livingstone)), along with multiple signal delivery elements 104 (shown as signal delivery elements 104a-104e) implanted at representative locations. For purposes of illustration, multiple signal delivery elements 104 are shown in FIG. 20 implanted in a single patient. In actual use, any given patient will likely receive fewer than all the signal delivery elements 104 shown in FIG. 20.

As shown in FIG. 20, the spinal cord SC is situated within a vertebral foramen F, between a ventrally located ventral body VB and a dorsally located transverse process TP and spinous process SP. Arrows V and D identify the ventral and dorsal directions, respectively. The spinal cord SC itself is located within the dura mater DM, which also surrounds portions of the nerves exiting the spinal cord SC, including the ventral roots VR, dorsal roots DR and dorsal root ganglia DRG. The dorsal roots DR enter the spinal cord SC at the dorsal root entry zone E, and communicate with dorsal horn neurons located at the dorsal horn DH. In one embodiment, the first and second signal delivery elements 104a, 104b are positioned just off the spinal cord midline M (e.g., about 1 mm offset) in opposing lateral directions so that the two signal delivery elements 104a, 104b are spaced apart from each other by about 2 mm. In other embodiments, a lead or pairs of leads can be positioned at other epidural locations, e.g., toward the outer edge of the dorsal root entry zone E as shown by a third signal delivery element 104c, or at the dorsal root ganglia DRG, as shown by a fourth signal delivery element 104d, or approximately at the spinal cord midline M, as shown by a fifth signal delivery element 104e, or near the ventral roots, as shown by a sixth signal delivery element 104f. In some embodiments, the leads are positioned near the exit of the ventral roots may be advantageous to modify ventral motor pools located in the gray matter. For example, modification of these ventral motor pools may treat spasticity, motor disorders and/or other disorders arising from the ventral motor pools.

In some embodiments, it may be advantageous to position one or more signal delivery elements 104 within the dura mater DM to target neural tissue and one or more glial cells present in the gray and white matter of the spinal cord SC. For example, as shown in the cross-sectional view of a spinal cord SC in FIG. 21, in some embodiments a first signal delivery element 104g and a second signal delivery element 104i are positioned along the spinal cord midline M on the dorsal and ventral sides of the spinal cord SC, respectively. In other embodiments, one or more signal delivery elements 104 can be positioned at other locations. For example, in some embodiments a first signal delivery element 104h and a second signal delivery element 104j are positioned off the spinal cord midline M on opposing lateral sides of the spinal cord SC. High frequency signals applied to the second signal delivery element 104j may be especially effective at reducing sympathetic outflow. In some embodiments, high frequency signals applied to the second signal delivery element 104j may treat heart failure, hypertension, complex regional pain syndrome, peripheral vascular disease, and other diseases where elevated sympathetic tone is implicated. In other embodiments, one or more signal delivery elements 104 may be positioned in other suitable locations within the subdural space. Additionally, in a particular embodiment, a physician may position one or more signal delivery elements in the epidural space and one or more signal delivery elements in the subdural space.

B. Brain and Vagal Nerve Locations

Figure 22:
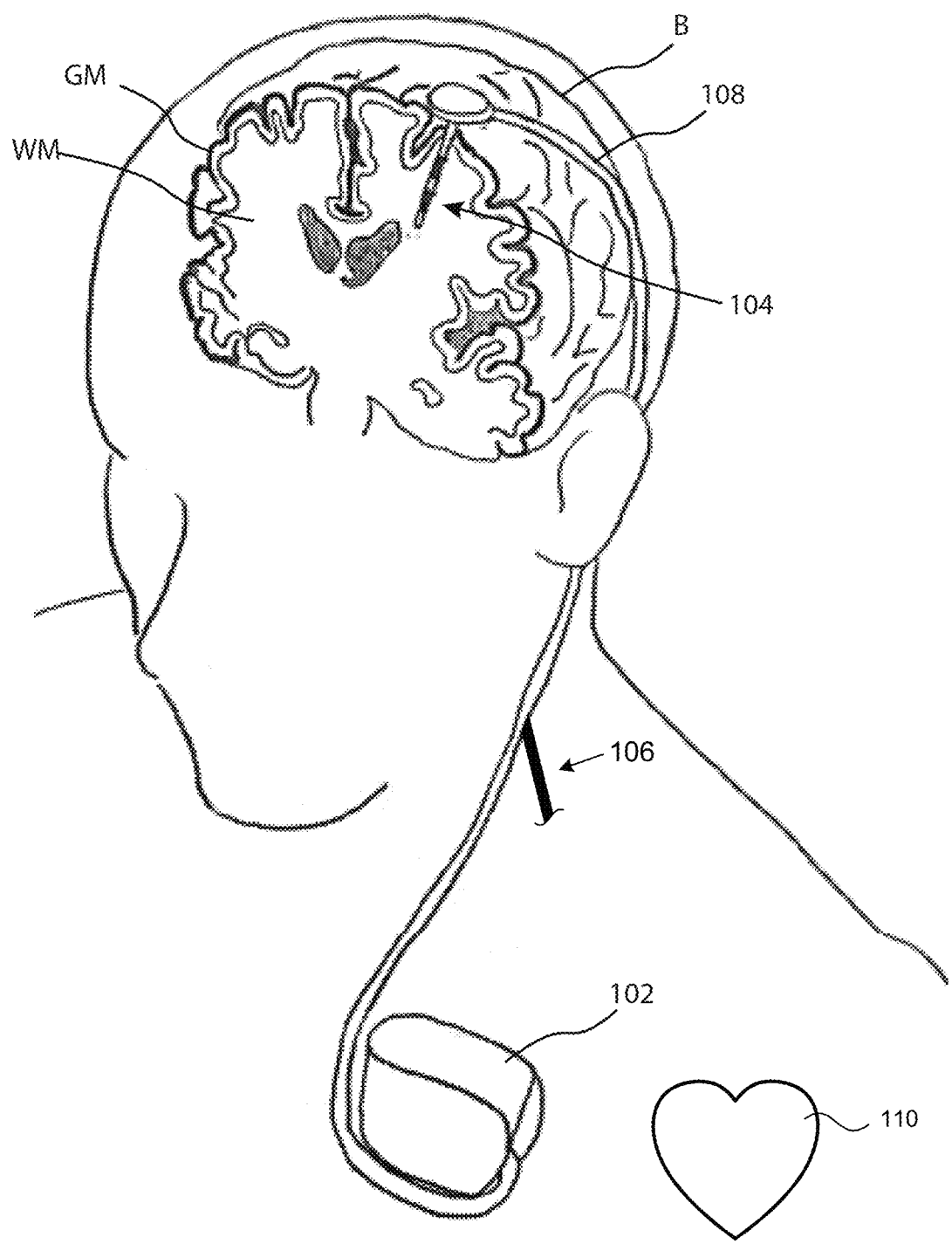
FIGS. 22-23 are partially schematic, cross-sectional illustrations of a patient's brain, illustrating representative locations for implanted signal delivery devices in accordance with several embodiments of the present technology.
Figure 23:
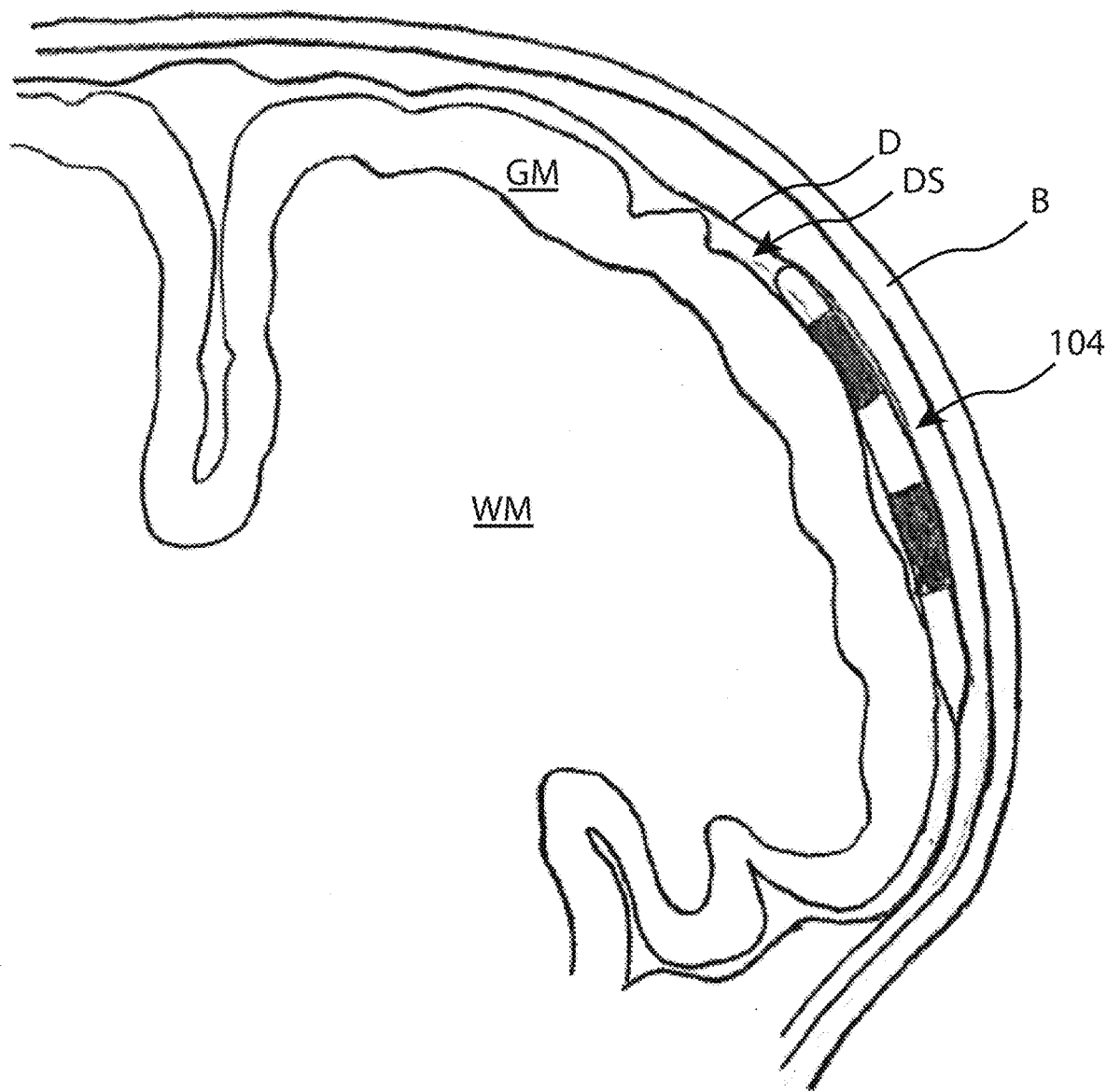

In some aspects of the present technology, one or more signal delivery elements 104 may be positioned within the patient's head, and any lobe of the cortex or deep brain can be stimulated. For example, FIG. 22 shows a signal delivery element 104 positioned within the white matter WM of the deep brain region, and FIG. 23 shows a signal delivery element 104 positioned within the subdural space DS in contact with a cortex of the brain. Examples of deep brain regions that may be stimulated include, for example, the anterior thalamus, the ventrolateral thalamus (Thal), the internal segment of globus pallidus (GPi), the substantia nigra pars reticulata (SNr), the subthalamic nucleus (STN), the external segment of globus pallidus (GPe), the neostriatum, cingulate, the cingulate gyrus, and others. Examples of veins providing access to the deep brain include the inferior sagittal sinus, pericallosal sinus, cavernous sinus, sphenoid sinus, temporal basal vein, and occipital veins. Examples of arteries providing access to the deep brain include any branches off the internal carotid or vertebral arteries. Examples of veins providing access to the SPG include the superficial temporal veins and the facial vein. Examples of arteries providing access to the SPG include the maxillary artery, descending palatine artery, and facial artery.

Examples of cortical regions of the brain that may be stimulated include the motor strip, the sensory strip, the pre-motor cortex, and other suitable regions. The signal delivery element(s) 104 can be delivered to any one of a number of vessels in order to place the electrodes adjacent the cortical tissue to be stimulated. Examples of veins providing access to the cortex include the superior sagittal sinus, any of the superior cerebral veins branching from the superior sagittal sinus (e.g., the lacuna, the frontopolar vein, the anterior frontal vein, the posterior frontal vein, the precentral vein, the central vein, the anterior parietal vein, the posterior parietal vein, and the occipital vein), the superior sylvian vein, the vein of Labbe, the vein of Trolard, the inferior sagittal sinus, and any inferior cerebral veins branching off of the inferior sagittal sinus, transverse sinus, and meningeal sinus. Examples of arteries providing access to the cortex include any of the branches off of the external carotid arteries, the maxillary arteries, or the meningeal arteries.

In any of the foregoing embodiments, the signal delivery element(s) 104 can be intravascularly introduced within the patient's head adjacent a selected brain region, or the signal delivery element can be non-vascularly introduced within the patient's head through, e.g., a burr hole drilled within the patient's cranium, or by performing a craniotomy. In those embodiments where the signal delivery elements are introduced intravascularly, the jugular and femoral veins can be used as intravascular access points from which the signal delivery element(s) can be delivered to the above-described veins, and the carotid or femoral arteries can be used as intravascular access points from which the signal delivery element(s) can be delivered to the above-described arteries. In those brain regions that are not adjacent to easily-accessible or navigable blood vessels, access to the treatment site may be accessed by non-vascular means, e.g., by penetrating the parenchyma for deep brain stimulation (as shown in FIG. 22), or by epidurally or subdurally placing the signal delivery element(s) 104 along the cortex for cortical simulation (as shown in FIG. 23). Thus, it will be appreciated that a combination of intravascular and non-vascular placement of the signal delivery element(s) 104 can be utilized in procedures involving multiple brain regions.

After the leads have been deployed within the spinal cord and/or the brain, a high frequency signal can be applied to directly affect the cellular membrane of cells. In some embodiments, cells are neurons, including quiescent neurons, spontaneously active neurons or neurons which vacillate between spontaneously active and quiescent. The high frequency signal can have any & suitable combination of the frequency, amplitude and pulse width parameter, discussion herein.

In other aspects of the present technology, one or more signal delivery elements 104 can be positioned within the patient's head, neck, chest or abdomen, and any portion of the vagus nerve can be stimulated. For example, FIG. 22 shows a portion of the vagus nerve 106 extending through the patient's neck near the surrounding carotid artery. Examples of portions of the vagus nerve that may be stimulated include, for example, the medulla oblongata, jugular foramen, carotid sheath, neck, chest and abdomen and others.

C. Cardiac and Other Locations

In yet other aspects of the present technology, one or more signal delivery elements 104 can be positioned within the patient's chest, and any suitable portion of the heart, any suitable tissue of the heart, and/or any suitable connected structure, such as an artery, a vein, and/or a nerve can be stimulated. For example, FIG. 22 schematically shows the heart 110 in the patient's chest. Examples of portions of the heart that may be stimulated include, for example, the right atrium, left atrium, right ventricle, atrioventricular septum, the cardiac skeleton, left ventricle, tricuspid valve, bicuspid valve (e.g., mitral valve), semilunar pulmonary valve, semilunar aortic value, and others. Further examples of portions of the heart that may be stimulated include, for example, the inner endocardium, middle myocardium, the outer epicardium, any tissue comprising a cardiomyocyte, any tissue comprising a pacemaker cell, and others. Examples of suitable connected structures include, for example, the aorta, right pulmonary artery, left pulmonary artery, right coronary artery, left coronary artery, superior vena cava, inferior vena cava, right pulmonary vein, left pulmonary vein, great cardiac vein, middle cardiac vein, small cardiac vein, anterior cardiac vein(s), accelerans nerve, the vagus nerve, and others.

In yet other aspects of the present technology, one or more signal delivery elements 104 can be positioned along the patient's spine or distributed within the patient's body to target specific sympathetic ganglia with high frequency. Examples of suitable structures include the sympathetic chain, the ciliary, the sphenopalatine, the submaxillary, the otic, the celiac, the superior mesenteric, the inferior mesenteric ganglia, as well as the innervation site of these ganglia at their target organs.

D. Further Embodiments

In any of the foregoing embodiments, aspects of the therapy provided to the patient may be varied within or outside the parameters used during the experimental testing and computational models described above, while still obtaining beneficial results for patients suffering neurogenic and/or other disorders. For example, the location of the lead body (and in particular, the lead body electrodes) can be varied over the significant lateral and/or axial ranges described above. Other characteristics of the applied signal can also be varied. For example, as described above, the signal can be delivered at a frequency of from about 1.5 kHz to about 100 kHz, and in particular embodiments, from about 1.5 kHz to about 50 kHz. In more particular embodiments, the signal can be provided at frequencies of from about 3 kHz to about 20 kHz, or from about 5 kHz to about 15 kHz, or from about 3 kHz to about 10 kHz. In still further embodiments, the frequency range can extend beyond 100 kHz, e.g., up to 1 MHz. The amplitude of the signal can range from about 0.1 mA to about 20 mA in a particular embodiment, and in further particular embodiments, can range from about 0.5 mA to about 10 mA, or about 0.5 mA to about 4 mA, or about 0.5 mA to about 2.5 mA. The pulse width (e.g., for just the cathodic phase of the pulses) can vary from about 10 microseconds to about 333 microseconds. In further particular embodiments, the pulse width can range from about 25 microseconds to about 166 microseconds, or from about 33 microseconds to about 100 microseconds, or from about 50 microseconds to about 166 microseconds. The specific values selected for the foregoing parameters may vary from patient to patient and/or from indication to indication and/or on the basis of the selected vertebral location. In addition, the methodology may make use of other parameters, in addition to or in lieu of those described above, to monitor and/or control patient therapy. For example, in cases for which the pulse generator includes a constant voltage arrangement rather than a constant current arrangement, the current values described above may be replaced with corresponding voltage values.

In still further embodiments, the duty cycle may be varied from the ranges of values described above, as can the lengths of the on/off periods. For example, it has been observed that patients can have therapeutic effects (e.g., pain reduction) that persist for significant periods after the stimulation has been halted. In particular examples, the beneficial effects can persist for 10-20 minutes in some cases, and up to several hours or even days in others. Accordingly, the simulator can be programmed to halt stimulation for periods of up to several hours, with appropriate allowances for the time necessary to re-start the beneficial effects. This arrangement can significantly reduce system power consumption, compared to systems with higher duty cycles, and compared to systems that have shorter on/off periods.

In any of the foregoing embodiments, the parameters in accordance with which the signal generator 102 provides signals can be adjusted during portions of the therapy regimen. For example, the frequency, amplitude, pulse width, and/or signal delivery location can be adjusted in accordance with a pre-set therapy program, patient and/or physician inputs, and/or in a random or pseudorandom manner. Such parameter variations can be used to address a number of potential clinical situations. Certain aspects of the foregoing systems and methods may be simplified or eliminated in particular embodiments of the present disclosure.

Certain aspects of the disclosure described in the context of particular embodiments may be combined or eliminated in other embodiments. For example, as described above, the trial period, operating room mapping process, and/or external stimulator may be eliminated or simplified in particular embodiments. Therapies directed to particular indications may be combined in still further embodiments. Further, while advantages associated with certain embodiments have been described in the context of those embodiments, other embodiments may also exhibit such advantages, and not all embodiments need necessarily exhibit such advantages to fall within the scope of the present disclosure. The following examples provide additional embodiments of the disclosure.

Several of the embodiments described above include modifying cell membrane potentials to achieve a therapeutic result. The result can be identified on a large scale by observing and/or recording a change in the patient's condition (e.g., a reduction in symptoms resulting from the target indication). The result can be identified on a smaller scale by conducting tissue-level and/or cellular-level testing. Representative techniques include electrophysiological and/or electromyographical testing to demonstrate changes in the activation threshold of particular cells and/or groups of cells.

To the extent the foregoing materials and/or any other materials incorporated herein by reference conflict with the present disclosure, the present disclosure controls.

The following examples provide further representative embodiments of the presently disclosed technology.

A first representative method for treating a patient includes reducing or eliminating pain, spasticity, epilepsy, and/or motor disorders by applying or directing application of an electrical signal to the patient via a signal delivery device, the electrical signal having a frequency of from about 1.5 kHz to about 100 kHz. Reducing or eliminating pain, spasticity, epilepsy, and/or motor disorders can be performed by directly inhibiting neuronal cellular activity via membrane potential hyperpolarization.

A second representative method for treating a patient includes reducing or eliminating pain by applying or directing application of an electrical signal to the patient via an implanted signal delivery device, the electrical signal having a frequency of from about 1.5 kHz to about 100 kHz, an amplitude of from about 0.4 mA to about 5 mA, and a pulse width of from about 10 µs to about 300 µs, wherein the electrical signal directly affects at least one constituent or characteristic of a cell membrane. In a further specific example, the at least one constituent or characteristic includes one or more of a structure of the membrane, a channel of the membrane or a protein of the membrane.

A third representative method for treating a patient includes hyperpolarizing quiescent neurons to inhibit activity that causes pain, by applying or directing application of an electrical signal to the patient via an implanted signal delivery device, the electrical signal having a frequency of from about 1.5 kHz to about 100 kHz, an amplitude of from about 0.4 mA to about 5 mA, and a pulse width of from about 10 µs to about 300 µs.

A fourth representative method for treating a patient includes inhibiting spontaneously active neurons to reduce or eliminate pain, by applying or directing application of an electrical signal to the patient via an implanted signal delivery device, the electrical signal having a frequency of from about 1.5 kHz to about 100 kHz, an amplitude of from about 0.4 mA to about 5 mA, and a pulse width of from about 10 µs to about 300 µs.

A fifth representative method for treating a patient includes reducing or eliminating pain by applying or directing application of an electrical signal to the patient via an implanted signal delivery device, the electrical signal having a frequency of from about 1.5 kHz to about 100 kHz, an amplitude of from about 0.4 mA to about 5 mA, and a pulse width of from about 10 µs to about 300 µs, wherein the electrical signal hyperpolarizes quiescent neurons, and wherein the electrical signal inhibits and/or hyperpolarizes spontaneously active neurons.

A sixth representative method for treating a patient includes reducing or eliminating the patient's disease state by applying or directing application of an electrical signal to the patient via an implanted signal delivery device, the electrical signal having a frequency of from about 1.5 kHz to about 100 kHz, an amplitude of from about 0.4 mA to about 5 mA, and a pulse width of from about 10 µs to about 300 µs, wherein the electrical signal directly affects the constituents of a cell membrane.

I claim:

1. A method for treating a patient, comprising:
   selecting a frequency value for an electrical signal to be delivered to the patient's spinal cord region based at least in part on a target level of neuronal hyperpolarization, the frequency value being in a frequency range of from about 5 kHz to about 100 kHz and having a positive correlation with neuronal hyperpolarization; and
   addressing a condition of the patient by delivering the electrical signal with the selected frequency value to the patient's spinal cord region to hyperpolarize at least some neurons in the patient's spinal cord region, wherein hyperpolarizing the at least some neurons inhibits neuronal activity of the at least some neurons.

2. The method of claim 1 wherein the electrical signal is a bipolar electrical signal.

3. The method of claim 1 wherein an individual neuron of the at least some neurons includes a cell body, an axon, and a dendrite, and wherein delivering the electrical signal includes preferentially delivering the electrical signal to the cell body.

4. The method of claim 1 wherein the at least some neurons are included in a target neural population that includes C-type fibers and A-type fibers, and wherein delivering the electrical signal includes preferentially delivering the electrical signal to the C-type fibers.

5. The method of claim 4 wherein preferentially delivering the electrical signal to the C-type fibers includes hyperpolarizing the C-type fibers without modulating the A-type fibers.

6. The method of claim 1 wherein delivering the electrical signal includes delivering the electrical signal from an epidural location.

7. The method of claim 1, further comprising interrupting the electrical signal for a period in a range from 5 milliseconds to 15 milliseconds to reduce and/or eliminate a rebound effect in the at least some neurons.

8. The method of claim 1 wherein inhibiting the neuronal activity includes inhibiting the neuronal activity of quiescent neurons.

9. The method of claim 1 wherein inhibiting the neuronal activity includes inhibiting the neuronal activity of spontaneously active neurons.

10. The method of claim 9 wherein the condition of the patient includes spasticity.

11. The method of claim 9 wherein the condition of the patient includes essential tremor.

12. The method of claim 9 wherein the condition of the patient includes cardiac arrhythmia.

13. The method of claim 1 wherein the selected frequency value is in a frequency range of about 5 kHz to about 15 kHz.

14. The method of claim 1 wherein the frequency is ramped to decrease and/or eliminate a rebound effect in the at least some neurons.

15. The method of claim 1 wherein the electrical signal has an amplitude, and wherein the amplitude is ramped to decrease and/or eliminate a rebound effect in the at least some neurons.

16. The method of claim 1 wherein hyperpolarizing at least some of the patient's neurons increases a membrane permeability of the at least some neurons.

17. The method of claim 16 wherein addressing the condition of the patient further includes delivering a drug to the patient after increasing the membrane permeability of the at least some neurons.

18. The method of claim 1 wherein delivering the electrical signal with the selected frequency value to the patient's spinal cord region hyperpolarizes the at least some neurons to the target level of neuronal hyperpolarization.

19. The method of claim 18, further comprising increasing a level of hyperpolarization of the at least some neurons relative to the target level by increasing the frequency of the electrical signal.

20. The method of claim 18, further comprising decreasing a level of hyperpolarization of the at least some neurons relative to the target level by decreasing the frequency of the electrical signal.

21. A method for treating a patient, comprising:
programming a signal generator to deliver an electrical signal to the patient's spinal cord region to hyperpolarize at least some neurons in the patient's spinal cord region, the electrical signal having a frequency value selected based at least in part on a target level of neuronal hyperpolarization, the frequency value being in a frequency range of from about 5 kHz to about 100 kHz and having a positive correlation with neuronal hyperpolarization, and wherein hyperpolarizing the at least some neurons inhibits neuronal activity of the at least some neurons.

22. A method for treating a patient, comprising:
selecting a frequency value for an electrical signal to be delivered to the patient's spinal cord region based at least in part on a target level of neuronal inhibition of spontaneously active neurons, the frequency value being in a frequency range of from about 5 kHz to about 100 kHz and having a positive correlation with neuronal inhibition; and
addressing a condition of the patient by delivering the electrical signal with the selected frequency value to the patient's spinal cord region to inhibit at least some spontaneously active neurons in the patient's spinal cord region.

23. The method of claim 22 wherein delivering the electrical signal with the selected frequency value to the patient's spinal cord region inhibits the at least some spontaneously active neurons to the target level of neuronal inhibition.

24. The method of claim 23, further comprising increasing a level of inhibition of the at least some neurons relative to the target level of inhibition by increasing the frequency of the electrical signal.

25. The method of claim 23, further comprising decreasing a level of inhibition of the at least some neurons relative to the target level of inhibition by decreasing the frequency of the electrical signal.

26. The method of claim 22, further comprising:
selecting an amplitude value for the electrical signal, the amplitude value being in an amplitude range of from about 0.1 mA to about 20 mA and having a positive correlation with neuronal inhibition,
wherein addressing the condition of the patient by delivering the electrical signal with the selected frequency value includes delivering the electrical signal at the selected amplitude value.

27. A method for treating a patient, comprising:
programming a signal generator to deliver an electrical signal to the patient's spinal cord region to inhibit at least some spontaneously active neurons in the patient's spinal cord region, the electrical signal having a frequency value selected based at least in part on a target level of neuronal inhibition of spontaneously active neurons in the patient's spinal cord region, the frequency value being in a frequency range of from about 5 kHz to about 100 kHz and having a positive correlation with neuronal inhibition.

* * * * *